US011126825B2

(12) United States Patent
Herold et al.

(10) Patent No.: US 11,126,825 B2
(45) Date of Patent: *Sep. 21, 2021

(54) NATURAL LANGUAGE INTERACTION FOR SMART ASSISTANT

(71) Applicant: Microsoft Technology Licensing, LLC, Redmond, WA (US)

(72) Inventors: Keith Coleman Herold, Seattle, WA (US); Oz Solomon, Maple (CA)

(73) Assignee: Microsoft Technology Licensing, LLC, Redmond, WA (US)

( * ) Notice: Subject to any disclaimer, the term of this patent is extended or adjusted under 35 U.S.C. 154(b) by 16 days.

This patent is subject to a terminal disclaimer.

(21) Appl. No.: 16/599,426

(22) Filed: Oct. 11, 2019

(65) Prior Publication Data

US 2020/0042839 A1 Feb. 6, 2020

Related U.S. Application Data

(63) Continuation of application No. 15/656,994, filed on Jul. 21, 2017, now Pat. No. 10,460,215.

(Continued)

(51) Int. Cl.
*G10L 15/00* (2013.01)
*G06K 9/00* (2006.01)
(Continued)

(52) U.S. Cl.
CPC ........ *G06K 9/00261* (2013.01); *A61B 5/0205* (2013.01); *A61B 5/0507* (2013.01);
(Continued)

(58) Field of Classification Search
CPC ....... G10L 15/22; G06F 16/338; G06F 40/35; G06F 40/56
See application file for complete search history.

(56) References Cited

U.S. PATENT DOCUMENTS 7,783,486 B2 * 8/2010 Rosser .................... G10L 15/22
704/270
8,885,882 B1 11/2014 Reale et al.
(Continued)

FOREIGN PATENT DOCUMENTS

CN   102760434 A   10/2012
CN   103209030 A    7/2013
(Continued)

OTHER PUBLICATIONS

"Non Final Office Action Issued in U.S. Appl. No. 15/832,656", dated Jan. 6, 2020, 9 Pages.
(Continued)

*Primary Examiner* — Daniel Abebe
(74) *Attorney, Agent, or Firm* — Alleman Hall Creasman & Tuttle LLP

(57) ABSTRACT

A method for natural language interaction includes recording speech provided by a human user. The recorded speech is translated into a machine-readable natural language input relating to an interaction topic. An interaction timer is maintained that tracks a length of time since a last machine-readable natural language input referring to the interaction topic was translated. Based on a current value of the interaction timer being greater than an interaction engagement threshold, a message relating to the interaction topic is delivered with a first natural language phrasing that includes an interaction topic reminder. Based on the current value of the interaction timer being less than the interaction engagement threshold, the message relating to the interaction topic is delivered with a second natural language phrasing that lacks the interaction topic reminder.

18 Claims, 13 Drawing Sheets

Related U.S. Application Data

(60) Provisional application No. 62/459,020, filed on Feb. 14, 2017, provisional application No. 62/482,165, filed on Apr. 5, 2017.

(51) Int. Cl.

| | | |
|---|---|---|
| G06K 9/72 | (2006.01) | |
| G06T 7/70 | (2017.01) | |
| G06K 9/62 | (2006.01) | |
| G06F 3/16 | (2006.01) | |
| G10L 15/18 | (2013.01) | |
| G06N 20/00 | (2019.01) | |
| G06T 7/292 | (2017.01) | |
| H04W 4/33 | (2018.01) | |
| H04W 4/029 | (2018.01) | |
| A61B 5/11 | (2006.01) | |
| A61B 5/117 | (2016.01) | |
| A61B 5/00 | (2006.01) | |
| G01S 5/28 | (2006.01) | |
| G06F 1/3206 | (2019.01) | |
| G06F 1/3231 | (2019.01) | |
| G06F 1/324 | (2019.01) | |
| G06F 3/01 | (2006.01) | |
| G06F 3/03 | (2006.01) | |
| G06F 21/32 | (2013.01) | |
| G10L 17/04 | (2013.01) | |
| G10L 17/08 | (2013.01) | |
| H04L 12/58 | (2006.01) | |
| H04L 29/08 | (2006.01) | |
| H04N 5/232 | (2006.01) | |
| H04N 7/18 | (2006.01) | |
| H04N 21/422 | (2011.01) | |
| H04N 21/442 | (2011.01) | |
| G07C 9/28 | (2020.01) | |
| G06F 40/35 | (2020.01) | |
| G06F 40/211 | (2020.01) | |
| G06T 7/73 | (2017.01) | |
| G06T 7/246 | (2017.01) | |
| G01S 5/18 | (2006.01) | |
| G06T 7/60 | (2017.01) | |
| G10L 15/22 | (2006.01) | |
| G10L 15/28 | (2013.01) | |
| H04R 1/40 | (2006.01) | |
| H04R 3/00 | (2006.01) | |
| H04N 5/33 | (2006.01) | |
| G10L 15/02 | (2006.01) | |
| G06N 5/02 | (2006.01) | |
| G06N 5/04 | (2006.01) | |
| G10L 15/06 | (2013.01) | |
| G10L 15/24 | (2013.01) | |
| G10L 15/26 | (2006.01) | |
| G10L 15/19 | (2013.01) | |
| G10L 15/08 | (2006.01) | |
| G10L 15/32 | (2013.01) | |
| G10L 25/51 | (2013.01) | |
| H04L 29/06 | (2006.01) | |
| A61B 5/0205 | (2006.01) | |
| A61B 5/0507 | (2021.01) | |
| G01S 13/72 | (2006.01) | |
| G06F 21/35 | (2013.01) | |
| G08B 13/14 | (2006.01) | |
| G06F 3/0482 | (2013.01) | |
| G06F 3/0484 | (2013.01) | |
| H04N 21/231 | (2011.01) | |
| G06F 3/0488 | (2013.01) | |
| G06F 16/70 | (2019.01) | |
| A61B 5/05 | (2021.01) | |
| G01S 5/16 | (2006.01) | |
| G01S 11/14 | (2006.01) | |
| G01S 13/86 | (2006.01) | |
| G06N 3/04 | (2006.01) | |
| G08B 29/18 | (2006.01) | |
| G10L 17/00 | (2013.01) | |
| G07C 9/32 | (2020.01) | |
| H04N 5/247 | (2006.01) | |
| G01S 13/38 | (2006.01) | |
| G01S 13/88 | (2006.01) | |

(52) U.S. Cl.
CPC ............ *A61B 5/117* (2013.01); *A61B 5/1113* (2013.01); *A61B 5/7475* (2013.01); *G01S 5/18* (2013.01); *G01S 5/28* (2013.01); *G01S 13/726* (2013.01); *G06F 1/324* (2013.01); *G06F 1/3206* (2013.01); *G06F 1/3231* (2013.01); *G06F 3/011* (2013.01); *G06F 3/017* (2013.01); *G06F 3/0304* (2013.01); *G06F 3/0482* (2013.01); *G06F 3/04842* (2013.01); *G06F 3/167* (2013.01); *G06F 21/32* (2013.01); *G06F 21/35* (2013.01); *G06F 40/211* (2020.01); *G06F 40/35* (2020.01); *G06K 9/00* (2013.01); *G06K 9/00214* (2013.01); *G06K 9/00255* (2013.01); *G06K 9/00288* (2013.01); *G06K 9/00295* (2013.01); *G06K 9/00342* (2013.01); *G06K 9/00362* (2013.01); *G06K 9/00711* (2013.01); *G06K 9/00771* (2013.01); *G06K 9/00973* (2013.01); *G06K 9/6254* (2013.01); *G06K 9/6255* (2013.01); *G06K 9/6289* (2013.01); *G06K 9/6296* (2013.01); *G06K 9/726* (2013.01); *G06N 5/025* (2013.01); *G06N 5/047* (2013.01); *G06N 20/00* (2019.01); *G06T 7/248* (2017.01); *G06T 7/292* (2017.01); *G06T 7/60* (2013.01); *G06T 7/70* (2017.01); *G06T 7/74* (2017.01); *G07C 9/28* (2020.01); *G08B 13/1427* (2013.01); *G10L 15/02* (2013.01); *G10L 15/063* (2013.01); *G10L 15/08* (2013.01); *G10L 15/18* (2013.01); *G10L 15/1815* (2013.01); *G10L 15/1822* (2013.01); *G10L 15/19* (2013.01); *G10L 15/22* (2013.01); *G10L 15/24* (2013.01); *G10L 15/26* (2013.01); *G10L 15/28* (2013.01); *G10L 15/32* (2013.01); *G10L 17/04* (2013.01); *G10L 17/08* (2013.01); *G10L 25/51* (2013.01); *H04L 51/02* (2013.01); *H04L 63/102* (2013.01); *H04L 67/12* (2013.01); *H04L 67/22* (2013.01); *H04N 5/23219* (2013.01); *H04N 5/332* (2013.01); *H04N 7/181* (2013.01); *H04N 7/188* (2013.01); *H04N 21/231* (2013.01); *H04N 21/42203* (2013.01); *H04N 21/44218* (2013.01); *H04N 21/44222* (2013.01); *H04R 1/406* (2013.01); *H04R 3/005* (2013.01); *H04W 4/029* (2018.02); *H04W 4/33* (2018.02); *A61B 5/05* (2013.01); *A61B 5/1118* (2013.01); *G01S 5/16* (2013.01); *G01S 11/14* (2013.01); *G01S 13/38* (2013.01); *G01S 13/867* (2013.01); *G01S 13/888* (2013.01); *G06F 3/0488* (2013.01); *G06F 16/70* (2019.01); *G06F 2203/0381* (2013.01); *G06K 2221/2111* (2013.01); *G06K 2209/09* (2013.01); *G06N 3/0445* (2013.01); *G06T 2207/10016* (2013.01); *G06T 2207/10024* (2013.01); *G06T 2207/20101* (2013.01); *G06T*

2207/30196 (2013.01); G06T 2207/30201 (2013.01); G06T 2207/30204 (2013.01); G06T 2207/30232 (2013.01); G07C 9/32 (2020.01); G08B 29/186 (2013.01); G10L 17/00 (2013.01); G10L 2015/0635 (2013.01); G10L 2015/088 (2013.01); G10L 2015/223 (2013.01); G10L 2015/225 (2013.01); G10L 2015/228 (2013.01); H04N 5/247 (2013.01); Y02D 10/00 (2018.01)

(56) References Cited

U.S. PATENT DOCUMENTS

| | | | |
|---|---|---|---|
| 9,070,366 | B1 | 6/2015 | Mathias et al. |
| 9,123,330 | B1 | 9/2015 | Sharifi et al. |
| 9,159,116 | B2 | 10/2015 | Plagemann et al. |
| 9,245,497 | B2 | 1/2016 | Pais et al. |
| 9,372,851 | B2 | 6/2016 | Hazen et al. |
| 9,669,296 | B1 | 6/2017 | Hibbert et al. |
| 9,747,896 | B2* | 8/2017 | Kennewick, Jr. ........ G10L 15/18 |
| 10,276,149 | B1 | 4/2019 | Liang et al. |
| 10,482,885 | B1 | 11/2019 | Moniz |
| 10,599,390 | B1 | 3/2020 | Brahmbhatt et al. |
| 2006/0067536 | A1 | 3/2006 | Culbert et al. |
| 2008/0015864 | A1* | 1/2008 | Ross ................. G10L 15/1822 704/275 |
| 2011/0119060 | A1 | 5/2011 | Aronowitz |
| 2011/0302535 | A1 | 12/2011 | Clerc et al. |
| 2013/0144616 | A1 | 6/2013 | Bangalore |
| 2013/0259456 | A1 | 10/2013 | Viswanathan |
| 2013/0304479 | A1 | 11/2013 | Teller et al. |
| 2014/0100997 | A1 | 4/2014 | Mayerle et al. |
| 2014/0156276 | A1 | 6/2014 | Nakano et al. |
| 2014/0160290 | A1 | 6/2014 | Wu |
| 2015/0032254 | A1 | 1/2015 | Ishiguro |
| 2015/0035976 | A1 | 2/2015 | Mayuzumi |
| 2015/0134547 | A1 | 5/2015 | Oikonomidis |
| 2015/0195666 | A1 | 7/2015 | Massey et al. |
| 2015/0220244 | A1 | 8/2015 | Vats et al. |
| 2015/0278199 | A1 | 10/2015 | Hazen et al. |
| 2015/0371639 | A1 | 12/2015 | Foerster et al. |
| 2016/0063989 | A1 | 3/2016 | Deleeuw |
| 2016/0110347 | A1* | 4/2016 | Kennewick, Jr. ... G06F 16/3329 704/9 |
| 2016/0171289 | A1 | 6/2016 | Lee et al. |
| 2016/0253310 | A1 | 9/2016 | Hazen et al. |
| 2016/0259623 | A1 | 9/2016 | Sumner et al. |
| 2016/0313868 | A1 | 10/2016 | Weng et al. |
| 2017/0169476 | A1 | 6/2017 | Nomula et al. |
| 2017/0186290 | A1 | 6/2017 | Li et al. |
| 2017/0206900 | A1 | 7/2017 | Lee et al. |
| 2017/0213157 | A1* | 7/2017 | Bugay ................. G06F 40/169 |
| 2017/0255450 | A1 | 9/2017 | Mullins et al. |
| 2017/0269975 | A1 | 9/2017 | Wood et al. |
| 2017/0286530 | A1 | 10/2017 | Paruchuri et al. |
| 2017/0357637 | A1 | 12/2017 | Nell et al. |
| 2018/0009118 | A1 | 1/2018 | Yamaga et al. |
| 2018/0090143 | A1 | 3/2018 | Saddler et al. |
| 2018/0107930 | A1 | 4/2018 | Aggarwal et al. |
| 2018/0314689 | A1 | 11/2018 | Wang et al. |
| 2018/0333862 | A1 | 11/2018 | Hayashi |
| 2020/0012906 | A1 | 1/2020 | Albadawi et al. |
| 2020/0104653 | A1 | 4/2020 | Solomon et al. |

FOREIGN PATENT DOCUMENTS

| | | |
|---|---|---|
| CN | 103262156 A | 8/2013 |
| CN | 104272709 A | 1/2015 |
| CN | 104423537 A | 3/2015 |
| CN | 105070288 A | 11/2015 |
| CN | 105389307 A | 3/2016 |
| CN | 105408891 A | 3/2016 |
| CN | 105611500 A | 5/2016 |
| CN | 106104517 A | 11/2016 |
| CN | 106157952 A | 11/2016 |
| CN | 106164921 A | 11/2016 |
| CN | 106340299 A | 1/2017 |
| WO | 2016043005 A1 | 3/2016 |
| WO | 2016157662 A1 | 10/2016 |

OTHER PUBLICATIONS

"Non Final Office Action Issued in U.S. Appl. No. 15/657,822", dated Feb. 6, 2020, 25 Pages.
"Final Office Action Issued in U.S. Appl. No. 15/646,871", dated Jan. 21, 2020, 23 Pages.
"Final Office Action Issued in U.S. Appl. No. 15/640,251", dated Jan. 30, 2020, 21 Pages.
"Non Final Office Action Issued in U.S. Appl. No. 16/005,470", dated Feb. 24, 2020, 11 Pages.
"Non Final Office Action Issued in U.S. Appl. No. 15/646,871", dated Jul. 1, 2020, 24 Pages.
"Final Office Action Issued in U.S. Appl. No. 15/657,822", dated Aug. 7, 2020, 22 Pages.
"Notice of Allowance Issued in U.S. Appl. No. 15/640,251", dated Jul. 31, 2020, 11 Pages.
"Final Office Action Issued in U.S. Appl. No. 16/005,470", dated Sep. 4, 2020, 15 Pages.
"Non Final Office Action Issued in U.S. Appl. No. 15/640,113", dated May 14, 2020, 13 Pages.
"Non Final Office Action Issued in U.S. Appl. No. 15/640,201", dated May 27, 2020, 11 Pages.
"Notice of Allowance Issued in U.S. Appl. No. 15/832,656", dated Apr. 22, 2020, 8 Pages.
"Notice of Allowance Issued in U.S. Appl. No. 15/832,672", dated Jun. 2, 2020, 11 Pages.
"Non Final Office Action Issued in U.S. Appl. No. 15/936,076", dated Apr. 15, 2020, 23 Pages.
"Office Action Issued in European Patent Application No. 18707800.1", dated Jun. 4, 2020, 4 Pages.
"Office Action Issued in European Patent Application No. 18708508.9", dated May 28, 2020, 6 Pages.
Sarikaya, Ruhi, "The Technology Behind Personal Digital Assistants: An Overview of the System Architecture and key Components", In Journal of IEEE Signal Processing Magazine, vol. 34, Issue 1, Jan. 11, 2017, pp. 67-81.
"Non Final Office Action Issued in U.S. Appl. No. 15/980,631", dated Sep. 18, 2020, 12 Pages.
"Office Action Issued in European Patent Application No. 18706104.9", dated Sep. 21, 2020, 4 Pages.
"Non Final Office Action Issued in U.S. Appl. No. 16/700,308", dated Sep. 25, 2020, 18 Pages.
"Non Final Office Action Issued in U.S. Appl. No. 15/640,251", dated Sep. 12, 2019, 21 Pages.
"Notice of Allowance Issued in U.S. Appl. No. 16/573,677", dated Nov. 6, 2019, 9 Pages.
"First Office Action and Search Report Issued in Chinese Patent Application No. 201880011578.3", dated Feb. 2, 2021, 12 Pages.
"First Office Action and Search Report Issued in Chinese Patent Application No. 201880011967.6", dated Feb. 2, 2021, 13 Pages.
"First Office Action and Search Report Issued in Chinese Patent Application No. 201880011970.8", dated Feb. 2, 2021, 15 Pages.
"First Office Action and Search Report Issued in Chinese Patent Application No. 201880012028.3", dated Feb. 2, 2021, 13 Pages.
"First Office Action and Search Report Issued in Chinese Patent Application No. 201880011885.1", dated Feb. 1, 2021, 16 Pages.
"Second Office Action Issued in Chinese Patent Application No. 201880011578.3", dated Jun. 28, 2021, 6 Pages.
"Second Office Action Issued in Chinese Patent Application No. 201880011967.6", dated Jun. 25, 2021, 6 Pages.
"Second Office Action Issued in Chinese Patent Application No. 201880012028.3", dated Jun. 25, 2021, 8 Pages.

* cited by examiner

NATURAL LANGUAGE INTERACTION FOR SMART ASSISTANT

CROSS REFERENCE TO RELATED APPLICATIONS

This application is a continuation from U.S. patent application Ser. No. 15/656,994 filed Jul. 21, 2017, which claims priority to U.S. Provisional Patent Application No. 62/459,020 filed Feb. 14, 2017, and to U.S. Provisional Patent Application No. 62/482,165 filed Apr. 5, 2017, the entirety of which are hereby incorporated herein by reference.

BACKGROUND

Interacting with computing systems via natural interactions, such as one or more of voice recognition, text, gesture recognition, motion detection, gaze detection, intent recognition, brain activity assessment, text, the state of a home automated device, etc., enables natural user interface experiences. As the volume of digital information and the numbers of computing devices increase, managing such natural user interaction interfaces to provide positive user experiences can prove challenging.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

A method for natural language interaction includes recording speech provided by a human user. The recorded speech is translated into a machine-readable natural language input relating to an interaction topic. An interaction timer is maintained that tracks a length of time since a last machine-readable natural language input referring to the interaction topic was translated. Based on a current value of the interaction timer being greater than an interaction engagement threshold, a message relating to the interaction topic is delivered with a first natural language phrasing that includes an interaction topic reminder. Based on the current value of the interaction timer being less than the interaction engagement threshold, the message relating to the interaction topic is delivered with a second natural language phrasing that lacks the interaction topic reminder.

DETAILED DESCRIPTION

The present disclosure relates generally to systems, methods and logical constructs for providing intelligent assistance to users. In some examples, a variety of sensor data may be utilized to intelligently determine the content and/or timing of messages communicated to users and/or the performance of actions. In some examples, human communications such as user commands and other utterances, may be received and processed. In some examples, a human communication may be parsed and analyzed to generate an indication of one or more user intentions associated with the communication. In some examples, data from one or more sensors also may be utilized to process the human communications and/or user intentions. Such processing of human communications can provide numerous benefits to the user, who can interact with a smart assistant device in a way that feels natural and conversational.

Figure 1:
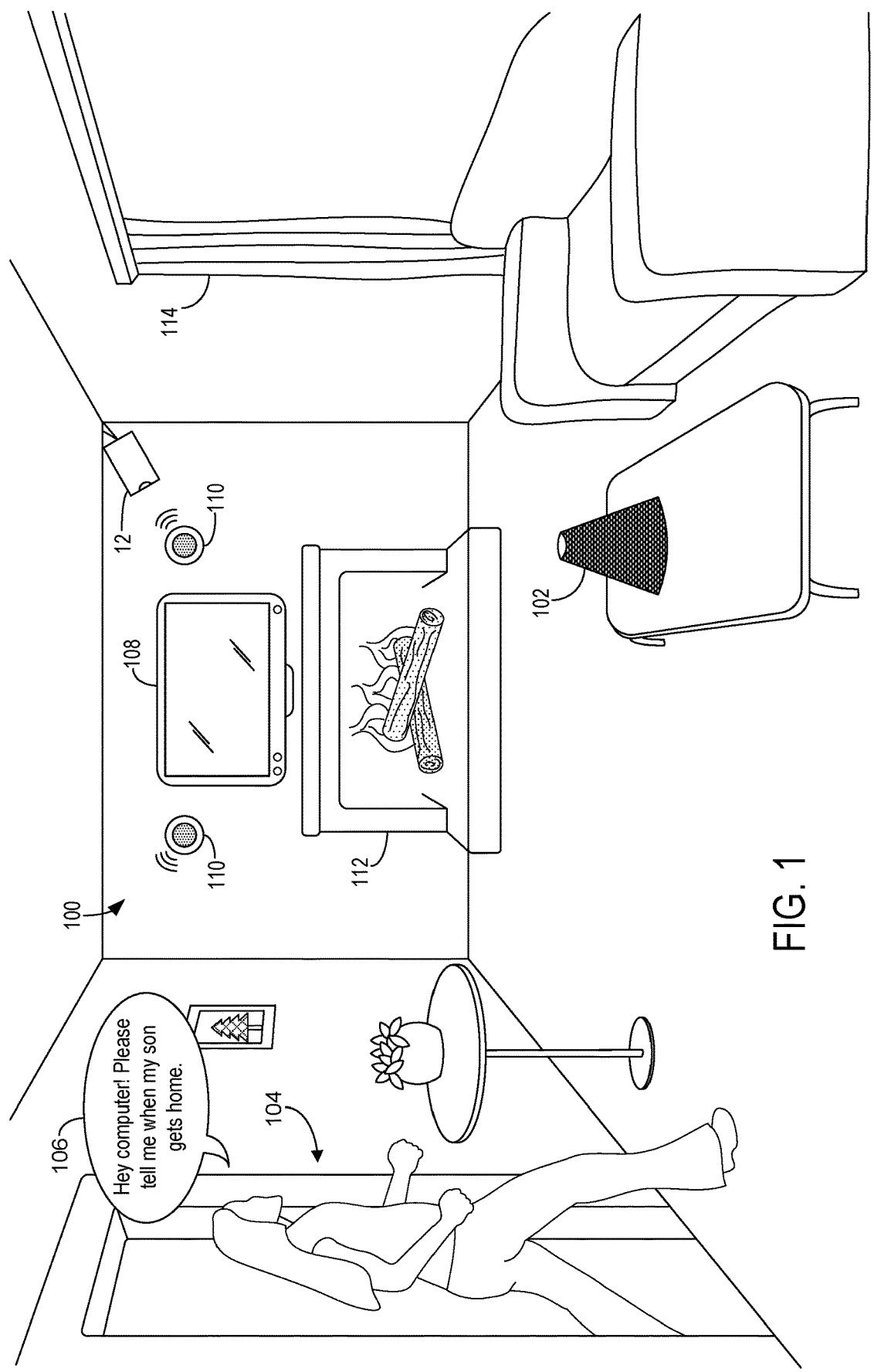
FIG. 1 shows an example environment with a smart assistant device in the form of an all-in-one computing device according to an example of the present disclosure.

FIG. 1 shows a living room 100 with one example of a smart assistant device in the form of an all-in-one computing device 102. As described in more detail below, in some examples computing device 102 may be configured to receive and process human communications from a human user 104. User 104 may utilize the smart assistant device for myriad functions. For example, the user may provide a spoken command, such as spoken command 106, to ask the smart assistant device to perform a variety of tasks. This may be translated by the device into a machine-readable natural language input, as will be described in more detail below. In this example, the user has asked the smart assistant device to notify her when her son gets home. Computing device 102 may, for example, utilize sensor data, such as audio and/or video data, to detect when another human enters the building, and determine whether the new human is the son of human user 104. The device may then deliver a message to human user 104, via speakers, a suitable display, and/or other suitable delivery method, informing her that her son has arrived.

The user may ask the system for information about a wide range of topics, such as the weather, personal calendar events, movie show times, etc. In some examples, the smart assistant device also may be configured to control elements in the living room 100, such as a television 108, speakers 110 of a music system, a gas fireplace 112, or motorized curtains 114.

The smart assistant device also may be utilized to receive and store messages and/or reminders to be delivered at an appropriate future time. Using data received from sensors, the smart assistant device may track and/or communicate with one or more users or other entities.

In some examples, the computing device 102 may be operatively connected with one or more other computing devices using a wired connection, or may employ a wireless connection via Wi-Fi, Bluetooth, or any other suitable wireless communication protocol. For example, the computing device 102 may be communicatively coupled to one or more other computing devices via a network. The network may take the form of a local area network (LAN), wide area network (WAN), wired network, wireless network, personal area network, or a combination thereof, and may include the Internet. Additional details regarding components and computing aspects of the computing device 102 are described in more detail below with reference to FIG. 13.

Figure 10:
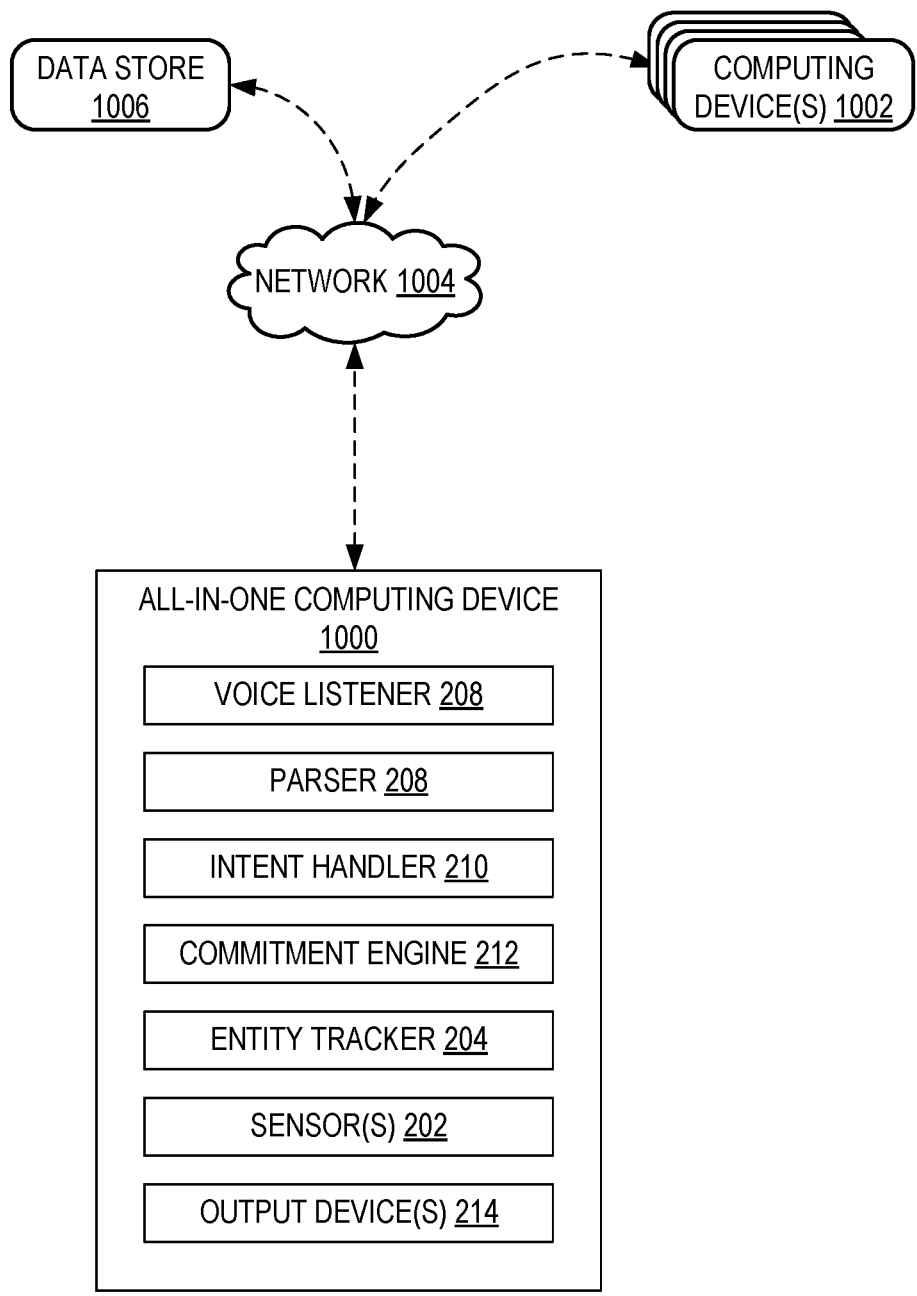
FIG. 10 schematically shows an all-in-one computing device that implements a smart assistant device according to examples of the present disclosure.
Figure 11:
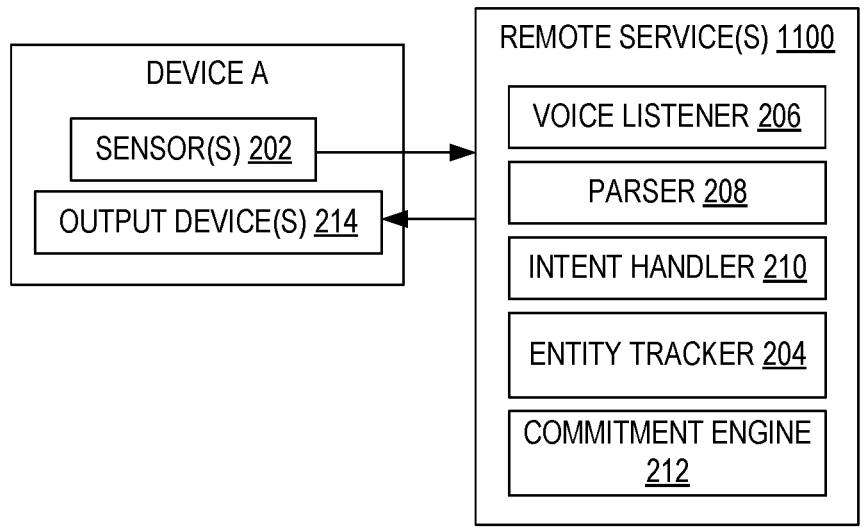
FIG. 11 schematically shows an example implementation in which one or more remote services perform functionality of the smart assistant device according to examples of the present disclosure.
Figure 12:
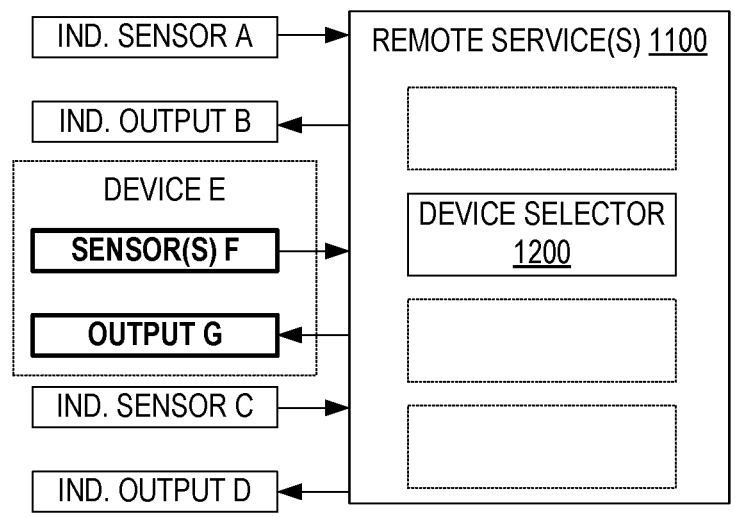
FIG. 12 schematically shows another example implementation in which one or more remote services perform functionality of a smart assistant device according to examples of the present disclosure.

It will be appreciated that the computing device 102 of FIG. 1 is merely one example implementation of the smart assistant device of the present disclosure. Additional example implementations across two or more devices are illustrated in FIGS. 10-12 and described in more detail below.

Figure 2:
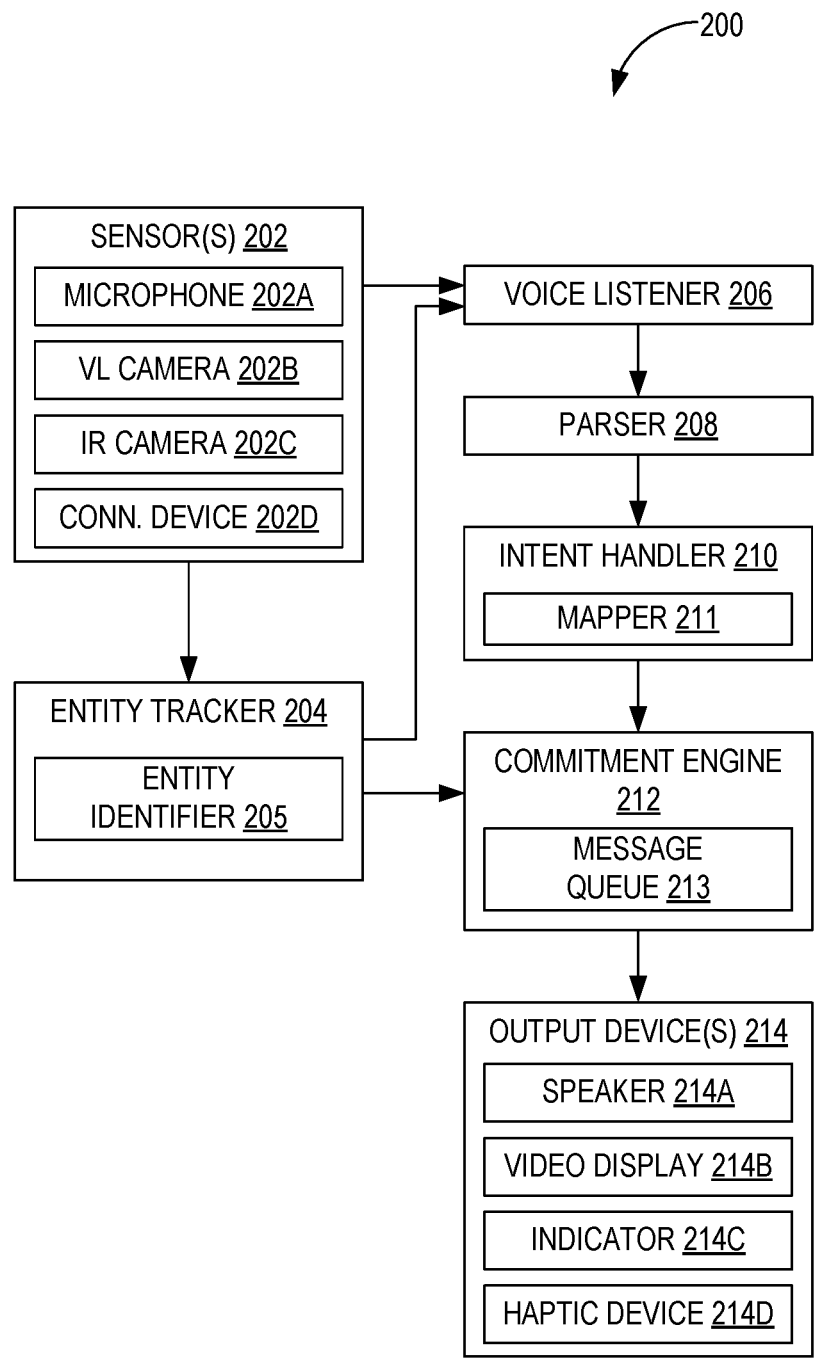
FIG. 2 schematically shows an example logical architecture for implementing a smart assistant device according to an example of the present disclosure.

FIG. 2 shows an example logical architecture for implementing a smart assistant device 200 capable of recognizing and responding to human communications according to examples of the present disclosure. As described in more detail below, in various examples the system 200 may be implemented in a single computing device, across two or more devices, in a cloud-supported network, and in combinations of the foregoing.

In this example the smart assistant device 200 includes at least one sensor 202, an entity tracker 204, a voice listener 206, a parser 208, an intent handler 210, a commitment engine 212, and at least one output device 214. In some examples the sensors 202 may include one or more microphones 202A, visible light cameras 202B, infrared cameras 202C, and connectivity devices 202D, such as Wi-Fi or Bluetooth modules. In some examples sensor(s) 202 may comprise stereoscopic and/or depth cameras, head trackers, eye trackers, accelerometers, gyroscopes, gaze detection devices, electric-field sensing componentry, GPS or other location tracking devices, temperature sensors, device state sensors, and/or any other suitable sensor.

The entity tracker 204 is configured to detect entities and their activities, including people, animals, or other living things, as well as non-living objects. Entity tracker 204 includes an entity identifier 205 that is configured to recognize individual users and/or non-living objects. Voice listener 206 receives audio data and utilizes speech recognition functionality to translate spoken utterances into text. Voice listener also may assign confidence value(s) to the translated text, and may perform speaker recognition to determine an identity of the person speaking, as well as assign probabilities to the accuracy of such identifications. Parser 208 analyzes text and confidence values received from voice listener 206 to derive user intentions and generate corresponding machine-executable language.

Intent handler 210 receives the machine-executable language representing user intentions from the parser 208, and resolves missing and ambiguous information to generate commitments. Commitment engine 212 stores commitments from the intent handler 210. At a contextually appropriate time, the commitment engine may deliver one or more messages and/or execute one or more actions that are associated with one or more commitments. Commitment engine 212 may store messages in a message queue 213 or cause one or more output devices 214 to generate output. The output devices 214 may comprise one or more of speaker(s) 214A, video display(s) 214B, indicator light(s) 214C, haptic device(s) 214D, and/or other suitable output devices. In other examples, output devices 214 may comprise one or more other devices or systems, such as home lighting, thermostats, media programs, door locks, etc., that may be controlled via actions executed by the commitment engine 212.

In different examples the voice listener 206, parser 208, intent handler 210, commitment engine 212, and/or entity tracker 204 may be embodied in software that is stored in memory and executed by one or more processors of a computing device. Additional details regarding the components and computing aspects of computing devices that may store and execute these modules are described in more detail below with reference to FIG. 13.

Detection and processing of human communications provided by a human user may in some cases be performed by voice listener 206 shown in FIG. 2. In some examples, voice listener 206 may receive audio data from the surrounding environment. In some examples, such as in computing device 102 of FIG. 1, the voice listener 206 may comprise a software module that is embodied in a standalone device that comprises one or more microphones. In other examples, the voice listener 206 software module may be stored in memory of a computing device that is located remotely from the user's environment, such as in a cloud-based service. In some examples, additional data from one or more other sensors may be received and utilized by the voice listener 206 in performing its functions that are described in more detail below.

The voice listener 206 may comprise speech recognition functionality that translates audio data of spoken utterances into text. As described in more detail below, the voice listener 206 also may assign a confidence value to one or more portions of translated text, such as individual speech components, words, phrases, etc.

Figure 3:
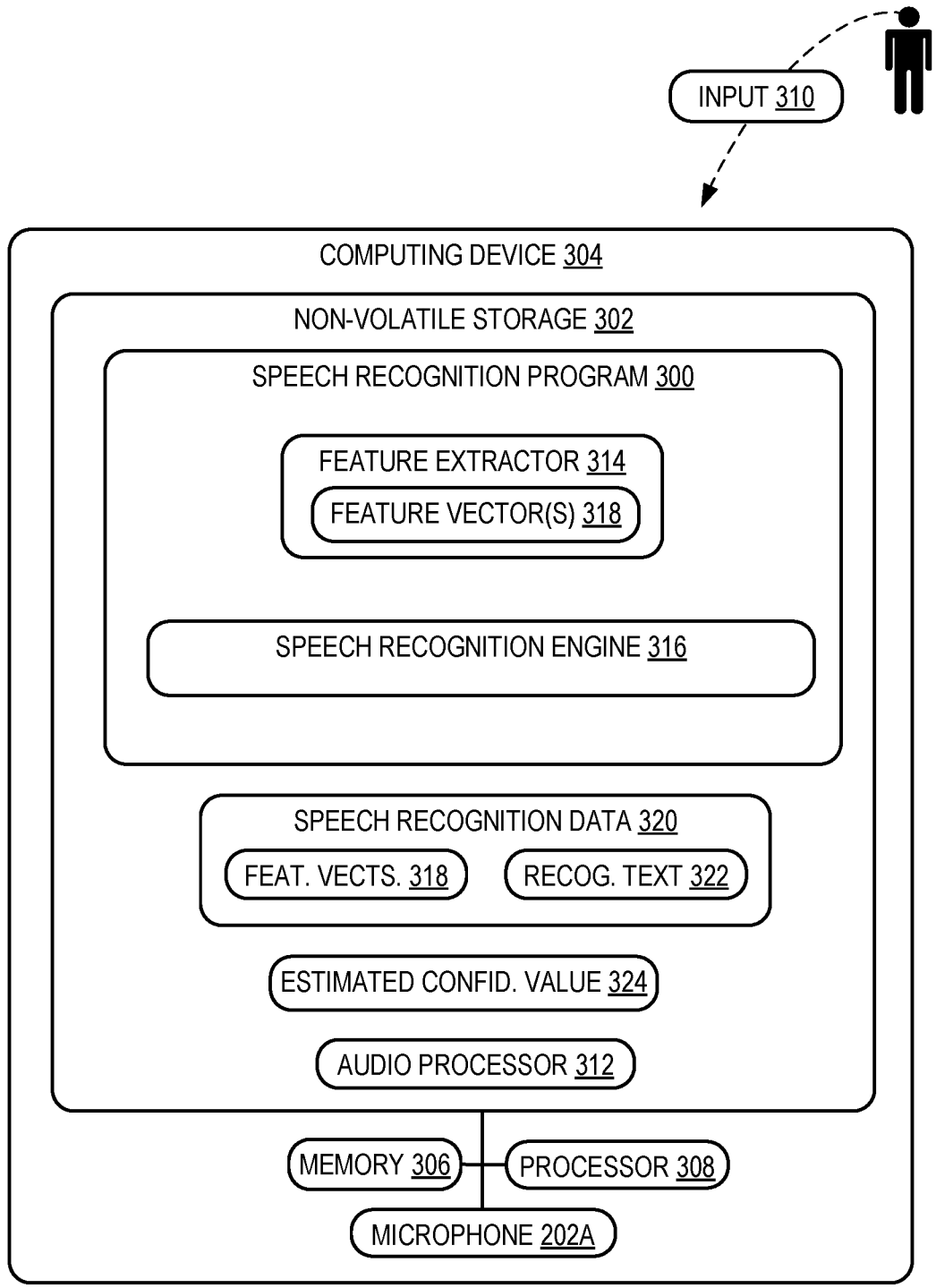
FIG. 3 schematically shows a speech recognition program that may be utilized by a voice listener according to an example of the present disclosure.

With reference now to FIG. 3, in some examples the voice listener 206 may comprise a speech recognition program 300 stored in non-volatile storage 302 of a computing device 304. The speech recognition program 300 may be loaded into memory 306 and executed by a processor 308 of computing device 304 to perform one or more of the methods and processes for speech recognition described in more detail below.

Audio input 310 in the form of speech may be captured by microphone 202A and processed by audio processor 312 to create audio data. Audio data from the audio processor 312 may be transformed by feature extractor 314 into data for processing by a speech recognition engine 316 of the speech recognition program 300.

Using the feature extractor 314 and speech recognition engine 316, the speech recognition program 300 may process feature vectors 318 and other speech recognition data 320 to generate recognized text 322. In other examples, any suitable techniques for matching feature vectors 318 to phonemes and/or other speech components may be utilized.

In some examples, the speech recognition program 300 may determine estimated confidence values 324 for one or more portions of the speech recognition data 320, such as individual speech components, words and phrases. An estimated confidence value 324 may define a statistical likelihood that the corresponding recognized text is accurate. As described in more detail below, the parser 208 of smart assistant device 200 may utilize such confidence values 324 in processing recognized text and determining a user's intent.

It will be appreciated that the foregoing descriptions of speech recognition techniques are merely examples, and that any suitable speech recognition technologies and processes may be utilized and are contemplated within the scope of the present disclosure.

With reference again to FIG. 2, in some examples the voice listener 206 may receive context information including associated confidence values from entity tracker 204. As described in more detail below, entity tracker 204 may determine an identity, position, and/or current status of one or more entities within range of one or more sensors, and may output such information to one or more other modules, such as voice listener 206, commitment engine 212, etc. In some examples, entity tracker 204 may interpret and evaluate sensor data received from one or more sensors, and may output context information based on the sensor data. Context information may include the entity tracker's guesses/predictions as to the identity, position, and/or status of one or more detected entities based on received sensor data. In some examples, the guesses/predictions may additionally include a confidence value defining the statistical likelihood that the information is accurate.

Additional details regarding components and computing aspects that may be used to implement voice listener 206 are described in more detail below with respect to FIG. 13.

With continued reference to FIG. 2, the voice listener 206 may send recognized text and corresponding confidence values to the parser 208. As described in more detail below, the parser 208 analyzes the text and confidence values to determine an intent of the user in speaking the received utterance. The parser 208 may translate the natural language text received from the voice listener 206 into a machine-executable language that represents a user's intention underlying the natural language.

In some examples the parser 208 may utilize a plurality of intent templates that each contain a plurality of slots that may be filled with words or terms received from the voice listener 206, or with words or terms that are based on other words received from the voice listener. In some examples where one or more slots are not filled, the parser 208 may fill these slots by examining a semantic meaning of one or more other words. For example, the smart assistant device 200 may tell a user, "You have 15 emails." The user may respond with an utterance, "OK, I'll go through them when I'm in the car." In response to the user's utterance, the parser 208 may fill a "commitment type" slot with the type "reminder", even though the word "reminder" itself was not in the user's utterance.

Taken together, the plurality of slots of an intent template define or otherwise characterize the intent of the user in speaking an utterance. In various different examples, the slots may comprise an action slot, a trigger slot, a commitment slot, a subject slot, a content slot, an identity slot, and various other types of slots. In some examples, each slot may embody one of three states: (1) missing information, (2) information present with unresolved ambiguity, and (3) information present with any ambiguity resolved.

Figure 4:
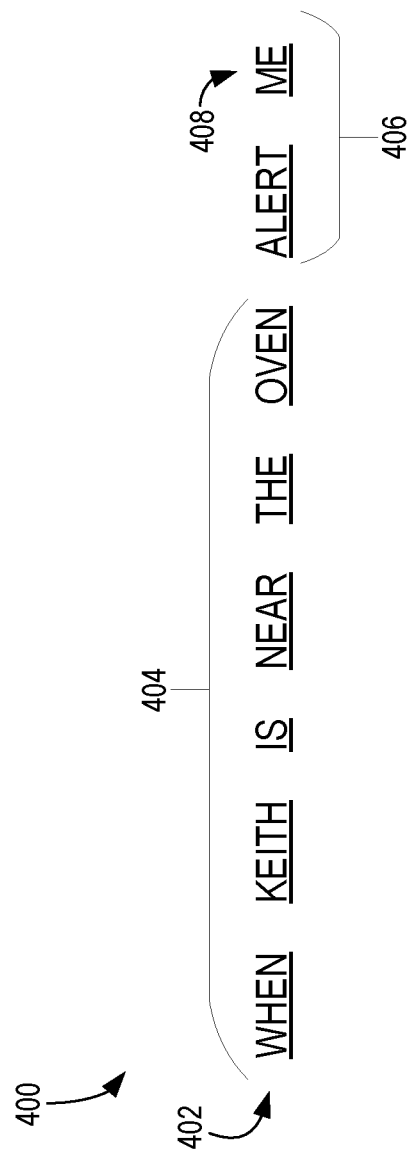
FIG. 4 shows of an intent template according to an example of the present disclosure.

One example of an intent template is a commitment intent template that corresponds to an add commitment intent. With reference now to FIG. 4, one example of a commitment intent template 400 is illustrated. In this example, the parser 208 may receive text phrase 402 from the voice listener 206 that reads "When Keith is near the oven alert me." The phrase "When Keith is near the oven" may be identified as a trigger 404. The phrase "alert me" may be identified as an action 406 that is to be carried out when the trigger is detected. As described in more detail below, in some examples the parser 208 may translate this text phrase 210 into machine-executable language that is passed to the intent handler 210 for further processing.

As noted above, the parser 208 may receive accuracy confidence values from the voice listener 206 that denote a likelihood that corresponding text is accurate. In some examples and as described in more detail below, the intent handler 210 also may receive entity confidence values that are associated with entity information. In some examples, such entity confidence values and other context information may be received via the entity tracker 204.

In the present example, the word "me" in phrase 402 fills a subject slot 408. In this example, the subject slot 408 corresponds to the person or other entity to be alerted when the trigger is detected. The word "me" may be received by the parser 208 with context information that associates this word to a particular person named Joe, and with an entity confidence value, such as 90%, that denotes a level of certainty that "me" is the person "Joe."

In some examples, the intended meaning of one or more words in an intent template may not be readily apparent. For example, in phrase 402 the meaning of the word "near" may be ambiguous, as "near" is a relative term. A variety of contextual factors may influence the intended meaning of "near" and the corresponding distance contemplated in this phrase. For example, where "Keith" is an infant, the intended meaning of "near" may be based on important safety concerns of the user speaking the phrase. Where "Keith" is the husband of the user, the intended meaning of "near" may be influenced less by safety concerns and more by convenience factors, which may lead to an associated distance that is different from the case where "Keith" is an infant. In another example, the distance intended to be conveyed in the phrase "near the oven" is likely different from the distance intended to be conveyed in the phrase "near the Statue of Liberty."

Accordingly, one or more words in an intent template may be ambiguous as passed to the intent handler 210. As described in more detail below, the intent handler 210 may utilize a plurality of techniques to resolve ambiguities and to fill in slots with missing information in an intent template.

In another example, the parser 208 may receive the text phrase "Play music with Fred" from the voice listener 206. In some examples, the phrase "Play music" is often interpreted to mean that a user wants to play digital music files via a media player. However, the use of the phrase "with Fred" following "Play music" is unusual, as people typically would not use this phrasing when their intent is to play music via a media player. The parser 208 may recognize this ambiguity and may generate a list of N-best intent templates that it determines are the statistically most probable intent templates corresponding to the user's actual intent. In some examples, the intent handler 210 may use additional context information to select an intent template from the list of N-best intent templates.

In some examples, the parser 208 may analyze received text to form a decision tree of the user's intent. In some examples, the parser 208 may generate If-Then statements (or rules) from the received text. Each If-Then statement may comprise a corresponding trigger and an action. Whenever the conditions of the trigger are satisfied, the action is performed. The resulting If-Then statements can perform a wide variety of tasks, such as home security ("text me if the motion detector in the back yard is activated"), home automation ("turn on the fireplace when I arrive home"), personal organization ("collect my email receipts for charitable donations into a spreadsheet"), health-related tasks ("remind me to eat protein if I run more than 7 miles"), and many others.

In some examples, the parser 208 may use an ensemble of two techniques to generate If-Then statements and/or derive an intent from the text received from the voice listener 206: (1) a recurrent neural network (RNN) architecture in the form of a long short-term memory (LSTM) network, and (2) a logistic regression model. In some examples, a graph long short term memory (graph LSTM) neural network may be utilized to extract from received text semantic meanings and relationships between words that are inherent to natural language. For example, text may be parsed using a graph LSTM neural network to extract cross-sentence n-ary relationships using several graph LSTM units arranged according to the syntactic relations of terms in the segment of text. These syntactic relationships between words may be tracked in the graph LSTM neural network to allow artificial intelligence and machine learning techniques to identify entities and their context within the text and from the grammatical structure in which they exist.

For example, context that identifies the nouns to which pronouns refer, the adverbs that modify given verbs, the prepositional phrases that affect a given word, etc., may be incorporated into the various words to enable more accurate searches of the contents of natural language documents. Additional descriptions of and examples of using graph LSTM neural networks to extract semantic meanings and relationships between words are provided in U.S. patent application Ser. No. 15/395,961, entitled GRAPH LONG SHORT TERM MEMORY FOR SYNTACTIC RELATIONSHIP DISCOVERY, filed on Dec. 30, 2016, the entire contents of which are incorporated herein by reference.

In some examples, the parser 208 may receive and process text to graph nodes (e.g., words, phrases, characters, etc.) and edges (e.g., dependency links between nodes) in individual phrases and across boundaries of phrases. In various examples, the graphing may include identifying one or more links (e.g., syntactic, semantic, co-reference, discourse, etc.) between nodes in the text. The links can include intra-phrase and inter-phrase links between nodes. For example, a link can represent a relationship between the root of one phrase and the root of an adjacent phrase. For another example, a link can represent a relationship between two words in a phrase, such as the modifier "Annie's" to the word "lunch." Additional details regarding graphing nodes and edges in phrases and across boundaries of phrases is disclosed in U.S. patent application Ser. No. 15/173,349, entitled RELATION EXTRACTION ACROSS SENTENCE BOUNDARIES, filed on Jun. 3, 2016, the entire contents of which are incorporated herein by reference.

Additional details regarding components and computing aspects that may be used to implement parser 208 are described in more detail below with respect to FIG. 13.

As described above, in some examples the parser 208 passes an intent template to the intent handler 210 for further processing. The intent handler 210 comprises a multi-step pipeline that may resolve ambiguous information and/or information that is missing from an intent template. As described in more detail below, the intent handler 210 may utilize a plurality of techniques to resolve ambiguities and fill in missing information slots with respect to an intent template. In some examples, the intent handler 210 may utilize domain-specific information and domain-specific reasoning to resolve ambiguities, complete missing information, and otherwise clarify an intent template to more closely correspond to the actual intent of the user.

In some examples, the intent handler 210 may glean knowledge regarding the user's intent by analyzing prior utterances of the user in a conversation history, and may utilize such insights to resolve ambiguities and add missing information to an intent template. Once the intent handler 210 has sufficiently clarified ambiguities and completed missing information, a corresponding commitment may be generated and passed to the commitment engine 212 for execution.

The intent handler 210 may be configured to process multiple intent templates that may comprise a conversation. For purposes of the present disclosure and as described in more detail below, a conversation may comprise a plurality of information and other data related to one or more exchanges between the user and the smart assistant device 200. In different examples, such information and data may comprise words and/or phrases spoken by a user, queries presented to the user by the smart assistant device 200, sensor data received from one or more sensors, context information such as person and/or identity information, etc.

As described in the use case examples provided below, the intent handler 210 may comprise a plurality of resolvers that translate intent templates and their associated data received from the parser 208 into internal data references. To address slots that comprise missing and/or unresolved information in an intent template, the intent handler 210 may utilize the plurality of resolvers in a multi-stage process. In some examples, each of the resolvers may be specifically programmed to handle issues associated with a particular intent template that may be received from the parser 208.

Examples of resolvers may include lookup resolvers that translate proper names, aliases, and other identifiers into internal representation data (for example, "Bob" is translated to an internal representation of the person "Bob", such as Bob's contact information). Examples of resolvers may include anaphoric resolvers that address expressions having an interpretation that depends upon an antecedent or postcedent expression in context (for example, "she" is translated to a slot representing "a personal identity of the pronoun 'she'"), and deixis resolvers that address words and phrases, such as "here" or "there", that cannot be fully understood without additional contextual information (for example, "there" may translated to a slot representing "where is there?"). In other examples, many other forms and types of resolvers may be utilized.

Figure 5:
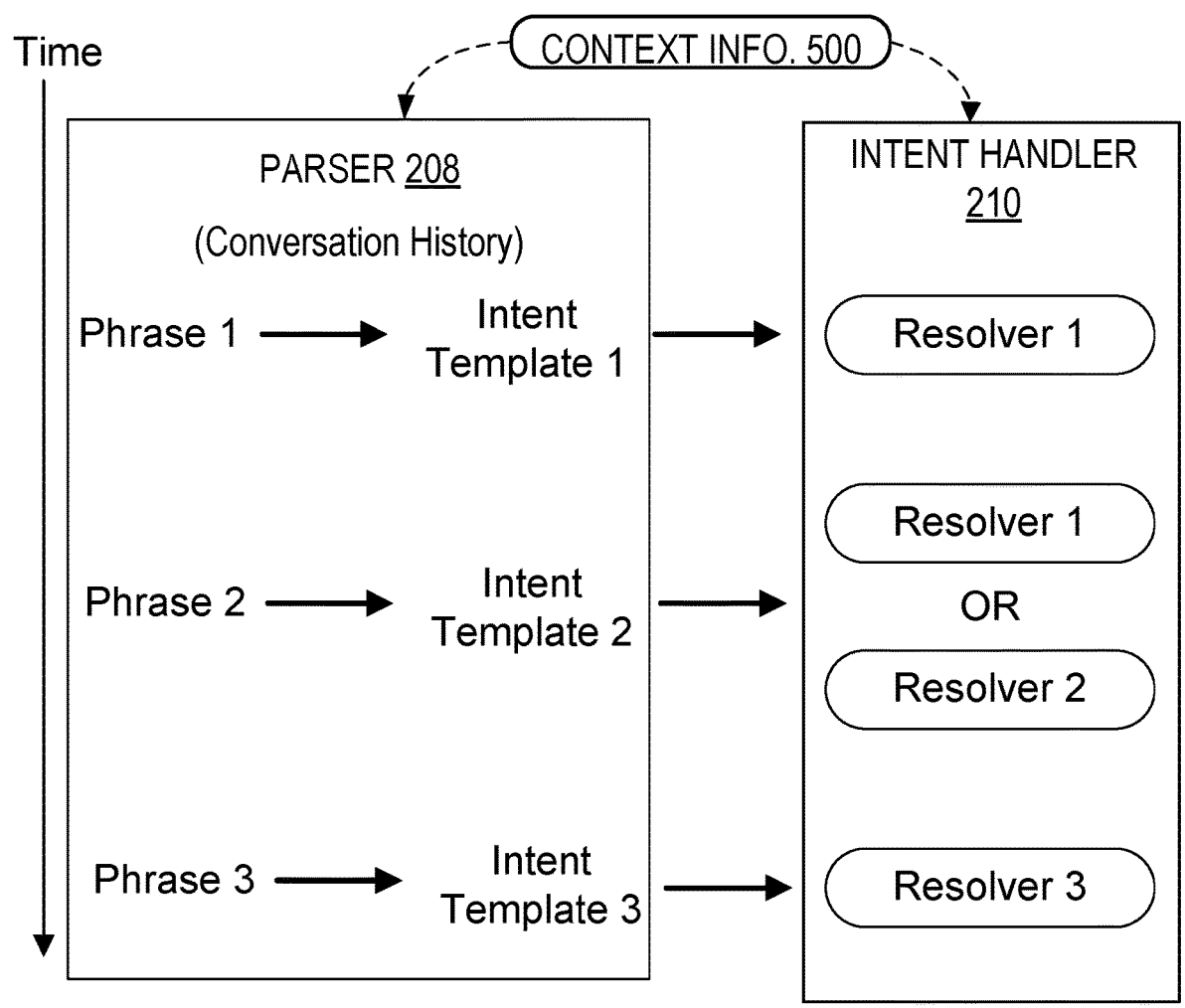
FIG. 5 schematically shows a parser and an intent handler processing a portion of a conversation according to an example of the present disclosure.

With reference now to FIG. 5, one example of the parser 208 and intent handler 210 processing a portion of a conversation is schematically illustrated. In this example, a first phrase 1 is parsed by the parser 208 into an intent template 1. The parser 208 provides intent template 1 to the intent handler 210, which utilizes a first resolver 1 to resolve ambiguities and/or missing information in this intent template. A second intent template 2 corresponding to a second phrase 2 is received from the parser 208. As described in more detail below, the intent handler 210 may analyze the intent template 2 along with context information 500 provided by entity tracker 204 to determine whether to utilize first resolver 1 or second resolver 2 to resolve the intent template 2. A third intent template 3 based on a third parsed phrase 3 may then be received by the intent handler 210. The intent handler 210 may utilize a third resolver 3 to resolve intent template 3. Additional details and use case examples of analyzing intent templates with resolvers are provided below.

In some examples the intent handler 210 may determine whether two or more intent templates should be fused or merged together to continue with an existing conversation path. If the intent handler 210 determines that the two or more intent templates should be fused together, then the intent handler may fuse the data associated with the two or more intent templates and continue following the existing conversation path with the fused data. If the intent handler 210 determines that the two or more intent templates should not be fused together, then a new topic may be started using the most recently received intent template.

As described in more detail below, where a slot of an intent template has missing information, the intent handler 210 may perform data gathering operations (such as to ask the user to clarify or provide information, or try to gather the information in another way) in order to populate information in the slot. Once each slot contains information, the intent handler 210 may determine if the information in each slot is unambiguous. For information identified as ambiguous, the intent handler 210 may apply one or more of a variety of techniques to resolve the ambiguity.

With reference again to FIG. 2, in some examples the intent handler 210 may comprise a mapper 211 that maps one or more system goals to a corresponding user intent(s). Examples of system goals may include clarifying ambiguities, acquiring additional information from a user, etc. In some examples, mapper 211 may internally rephrase system goals as user intents or goals. For example, mapper 211 may map information the system needs, such as information to resolve an ambiguous intent, to a user intent that the user would have triggered in providing that information. In other words, mapper 211 may map information to the intent that would have been resolved from an utterance that a user would have spoken in order to generate the intent. In some examples, mapper 211 may map a system goal to a word or phrase the user would have said to generate the same outcome.

In some examples, where the system needs information from a user to resolve a user intent, the system may internally cue a state that is equivalent to the state the system would have been in if the user had provided input (such as an utterance) containing all the components of the intent except for the needed information. In other words and in some examples, the system may assume that the user has already provided more input, with that input missing only one or more specific slot(s) corresponding to the needed information. In this manner, the intent handler 210 may continually utilize whatever user input is provided. In some examples, this allows the system to reuse components, such as intent templates. Accordingly and in these examples, by causing the intent handler 210 to assume that user intents (versus system goals) are driving its operation, the system may internally reuse corresponding logic and may understand such user intents with greater depth and richness.

In some examples, the system may have a goal of acquiring information from a user to proceed with deriving a user intent. In a first example, a user may speak two utterances: "Book me a flight to California tomorrow; The flight needs to be to San Francisco." In the first utterance, the user indicates an intent to book a flight, and in the second utterance the user narrows the intent to a flight to San Francisco. In both utterances, a user intent is specified.

In another example, the user speaks a first utterance "Book me a flight tomorrow." The system may respond with a query "Where do you want to fly to?" The user may then respond, "To San Francisco." Upon generating the system query, the mapper 211 may map the intent handler's goal (acquiring information of the user's destination) to a user intent. For example, the mapper 211 may presume that the user is about to provide this information as if it were the user's intent.

In some examples, by configuring the mapper 211 to presume that a user intent is driving its operation, the system may minimize the code to perform these operations and reuse corresponding logic. In this manner, the system may understand such user intents with greater depth and richness. Accordingly, in these examples the system may utilize code for the intent handler 210 and mapper 211 that comprises a user-intent only system, as opposed to utilizing multiple specialized pieces of code to manage all ambiguities and otherwise handle multiple corresponding tasks and discrete situations.

Additional details regarding components and computing aspects that may be used to implement intent handler 210 are described in more detail below with respect to FIG. 13.

Figure 6A:
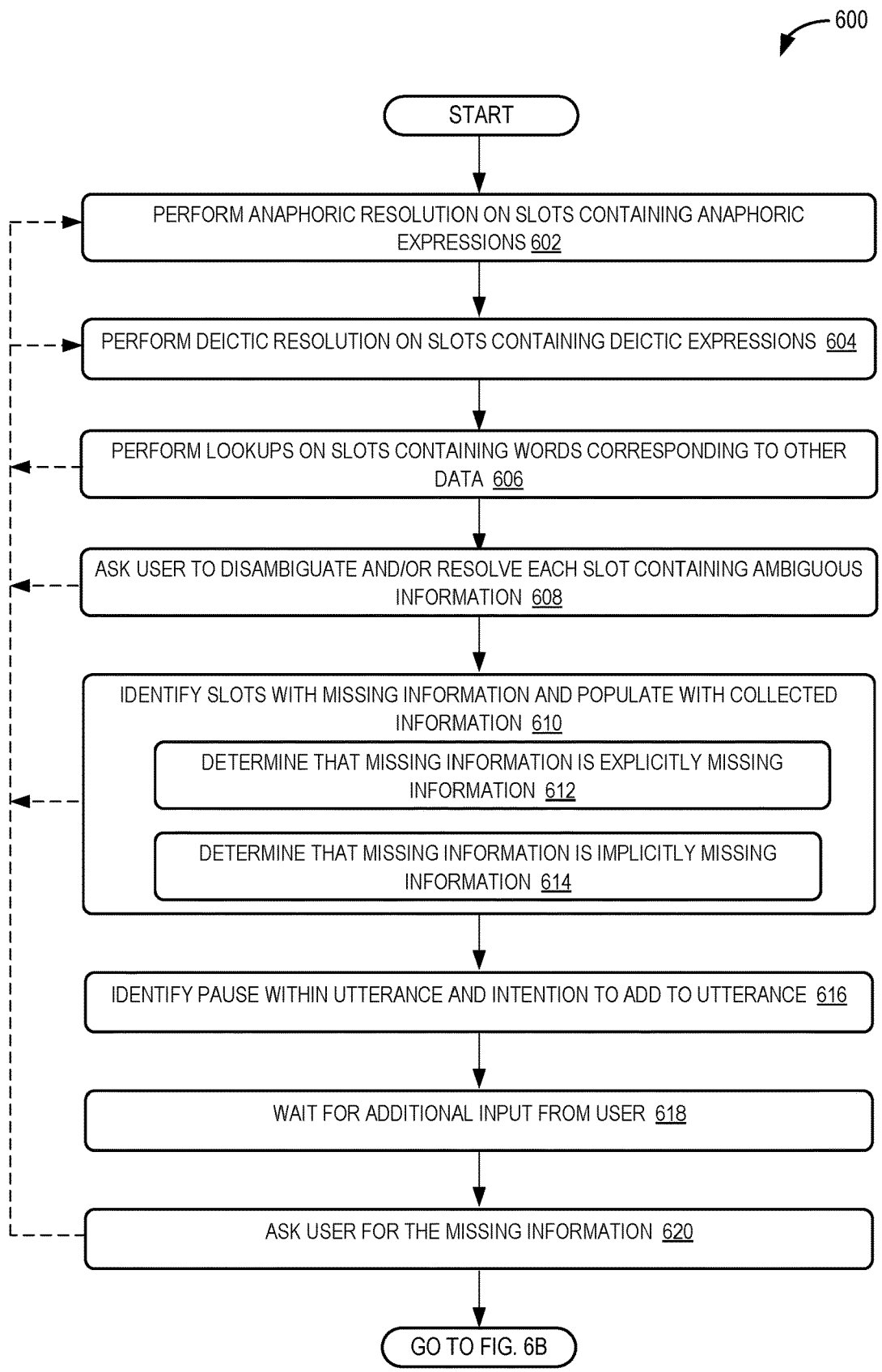
FIGS. 6A and 6B show a method for addressing missing and/or unresolved information in an intent template according to examples of the present disclosure.
Figure 6B:
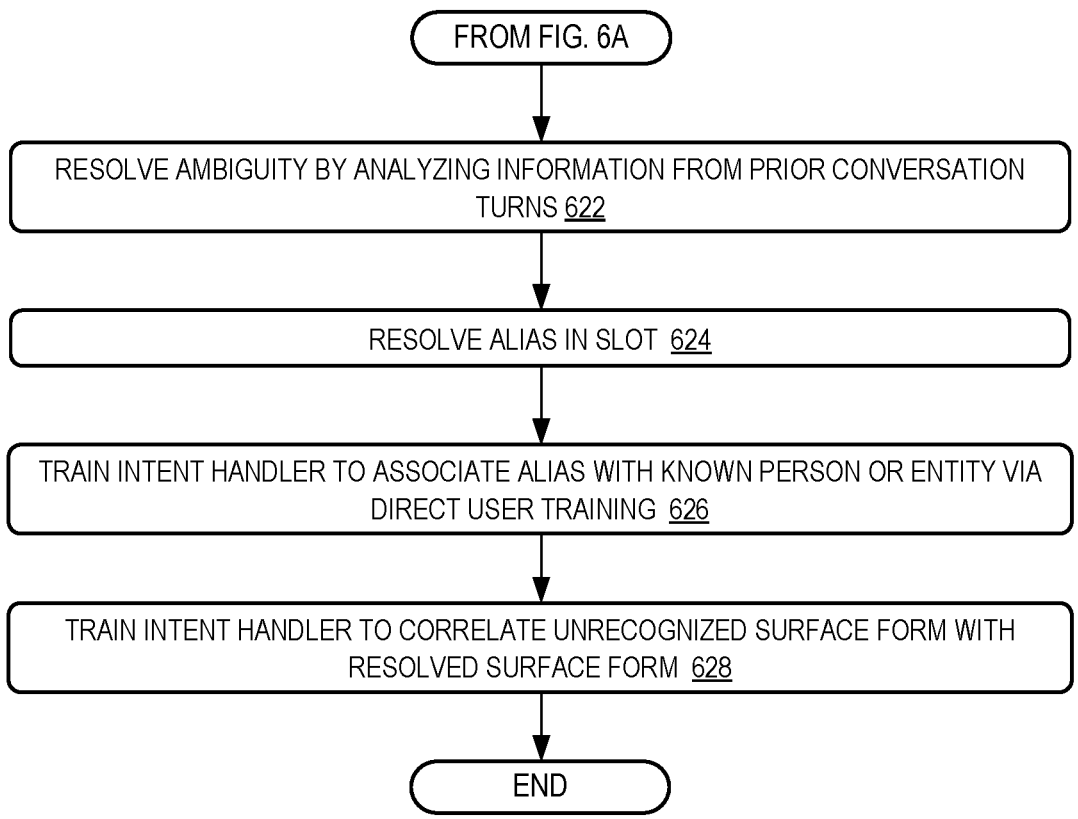

With reference now to FIGS. 6A and 6B, a flow chart of a method 600 for addressing missing and/or unresolved information in an intent template according to examples of the present disclosure is provided. The following description of method 600 is provided with reference to the software and hardware components described herein. It will be appreciated that method 600 also may be performed in other contexts using other suitable hardware and software components.

Additionally, while the blocks of method 600 are described and illustrated in a particular sequence, in different examples the order of execution may vary. In some examples one or more of the blocks may not be performed. In some examples, context information 500 from the entity tracker 204 may be utilized to determine an order of execution and/or which block to execute next.

With reference to FIG. 6A, at 602 the method 600 may include performing anaphoric resolution on slots that contain an anaphor or a cataphor. For example, in the phrase "When he is near the oven alert me", the word "he" is an anaphoric expression that refers to a person who was referenced earlier in the conversation. Additionally and as described in more detail below, by understanding and resolving the intent of the user via intent template(s) received from the parser 208, the intent handler 210 may augment this anaphoric resolution process with one or more other techniques, such as grounding and repair techniques described in more detail below, to more accurately determine the person who corresponds to an anaphoric expression.

At 604 the method 600 may include performing deictic resolution on slots that contain words that cannot be fully understood without additional contextual information. Examples of deictic expressions include words having a fixed semantic meaning and a denotational meaning that varies depending on time and/or place. For example, in the phrase "When he is near the oven alert me", the word "near" is a deictic expression whose meaning depends on contextual information. Additionally and as with anaphoric expressions, the intent handler 210 may augment its deictic resolution process with one or more other techniques, such as grounding and repair techniques, to clarify the intended meaning of the deictic expression.

In some examples, deictic resolution may be performed using data from one or more sensors, such as captured image data, audio data, position information, etc. For example, when a user points at an oven, image data showing the user's finger pointing at the oven may utilized by the entity tracker 204 to identify the oven and to determine that the user is pointing at the oven. While pointing the user may speak the utterance "Let me know when this gets hot." Using this information, the intent handler 210 may resolve the word "this" into "oven", and more particularly into the oven at which the user is pointing.

In another example, a user may speak "If my child comes in here let me know." The system may use location data of the user to resolve the word "here" into the current location of the user. In another example, two people walk into the room, and one person asks the system: "Do we have any messages?" Using sensory information, such as image data and/or audio data to identify both people, the system may perform deictic resolution to resolve "we" to the identities of the two people in the room.

At 606 the method 600 may include performing lookups for slots containing words that correspond to other data available to the intent handler 210. Examples of other data that may be available to the intent handler 210 include contact information, social graph data, calendar information, email data, photo metadata, and the like. Information accessed in performing such lookups may be populated in a slot to replace the word(s) presently occupying the slot. For example, in the phrase "Tomorrow remind me to drop the car at autodealer1", the word "autodealer1" may correspond to the auto repair shop where the user regularly has her car repaired. "Autodealer1" may be represented by a contact entry in the user's contact database. Accordingly, the intent handler 210 may locate such contact entry and may utilize the "Autodealer1" contact data for the word "autodealer1" in the intent template.

At this point, the method 600 may return to 602 and/or 604 to perform anaphoric resolution and/or deictic resolution, as needed, on information populated in a slot. Additionally, the intent handler 210 may augment its lookup process with one or more other techniques, such as grounding and repair techniques, to clarify the intended person or entity that corresponds to the information currently present in the slot.

At 608 the method 600 may include asking the user to disambiguate and/or resolve one or more slots containing ambiguous information. For example, where a user asks the system to "Call Patrick", and the user's contacts database includes a Patrick Doe and a Patrick Smith, the system may ask the user, "Which Patrick would you like to call, Patrick Smith or Patrick Doe?"

At 610 the method 600 may include identifying slots with missing information and populating these slots with collected information. Various techniques may be utilized to generate and/or retrieve such information. For example and as described in more detail below, slots with missing information may be treated differently depending upon whether the information is determined to be explicitly missing or implicitly missing.

For example, at 612 the method 600 may include determining that the missing information is explicitly missing information. In one example, by analyzing a text phrase the intent handler 210 may determine that the user's utterance suggests that information for a particular slot should be provided in the utterance. Where such information is missing, the information may be determined to be explicitly missing information. For example, consider the phrase "When Gary comes into the room with the others introduce." The intent handler 210 may determine that this phrase comprises a content slot corresponding to the subject of the verb "introduce", and that this content slot is missing information. In this example, the context of the phrase comprises the words that precede "introduce", these words' order and meaning, the factor that the phrase ends with the word "introduce" without naming the subject of the introduction, and the factor that the phrase constitutes a grammatically incomplete sentence.

The intent handler 210 may determine that this context does not resolve the ambiguity associated with this missing information. For example, while the user may be intending to introduce Gary to the others, other intentions are also possible (such as introducing one of the others to Gary). Accordingly, the intent handler 210 determines that the ambiguity associated with this missing information cannot be presently resolved. Given this ambiguity and as described in more detail below, the intent handler 210 may use one or more other techniques (such as querying the user, "Whom do you want to introduce?") to collect the missing information. In some examples as described in more detail below, the intent handler 210 may wait for the receipt of additional user input before querying the user. In some examples, additional information from the entity tracker 204 may be utilized to resolve the ambiguity and collect the missing information.

In some examples, where information for a trigger slot or an action slot of a commitment is missing, and based at least in part on context information 500 generated by the entity tracker 204, the intent handler 210 may proactively propose an action to the user. In one example, a user may speak the utterance "Alice." The intent handler 210 may receive an intent template with an empty action slot and a trigger slot partially completed with the name "Alice." The context information 500 may include an identity prediction with 85% confidence that "Alice" corresponds to the "Alice Jones" in the user's contact database. The context information 500 also may include a location prediction with 95% confidence that Alice Jones is located in the basement laundry room of the user's house. Based at least in part on this context information 500, the intent handler 210 may proactively ask if the user would like to communicate with Alice Jones, such as via an in-home intercom system.

At 614 the method 600 may include determining that the missing information is implicitly missing information. In one example, the intent handler 210 may determine that a user did not intend to provide information that is missing from a particular slot. Such missing information may be determined to be implicitly missing information. For example, consider the phrase "When Gary walks into the kitchen say Hello." The intent handler 210 may determine that the command "say Hello" corresponds to the user saying Hello to another person. Accordingly, the intent template corresponding to this phrase may comprise a content slot that follows the words "say Hello" and which normally contains the name or other identifier of the person the user intends to say Hello to (e.g., "Say Hello to Suzanne").

In this example, because the phrase ended with the word "Hello", such content slot is missing information that identifies the person intended. The context of this phrase comprises the words that precede "Hello", these words' order and meaning, and the factor that the phrase constitutes a grammatically complete sentence. Given this context, the intent handler 210 infers that the user intends for the command "say Hello" to apply to Gary. In other words, the context associated with this phrase indicates that the content slot following the words "say Hello" should be filled with "Gary." In this manner, the intent handler 210 may resolve this particular ambiguity associated with the missing information without querying the user for additional input. After populating a slot with missing information as described above, the method 600 may return to 602 and 604 to perform anaphoric resolution and/or deictic resolution, as needed, on the information populated in the slot.

In some examples and as noted above, the intent handler 210 may query the user for information that is missing from a slot. For example, the intent handler 210 may broadcast a spoken word query to the user via a speaker of a mobile phone. In some examples, however, information missing from a slot may be the result of an intended or unintended pause by the user that interrupts the user before the user completes her utterance. Accordingly and at 616, in some examples the method 600 may include identifying a pause within an utterance from a user along with an intent of the user to continue speaking and add to the utterance.

For example, a user may pause mid-utterance to think about what she should say next. In other examples, a user may be interrupted mid-utterance by an external event, such as another person speaking, distracting activity from the user's environment such as a loud noise or bright light, or a variety of other external activities.

In one example and with reference to the description above for identifying explicitly missing information, the phrase "When Gary comes into the room with the others introduce" may be determined to comprise a content slot that corresponds to the subject of the verb "introduce" and is missing information. Based on the empty content slot, other aspects of the phrase, and/or the context in which it is spoken, the intent handler 210 may identify a pause at the end of this phrase along with a predicted intent of the user to continue speaking and to add a subject to the verb "introduce."

At 618 and in response to identifying the pause, the method 600 may include waiting for additional input from the user before asking the user for more information. In some examples, the intent handler 210 may wait for a predetermined period of time, such as 1 second, 2 seconds, or other length of time that does not create a negative user experience for the user. In this manner, the system may avoid interrupting the user mid-utterance where the user intends to begin speaking again and to add to the utterance.

At 620 the method 600 may include querying the user for information missing from a slot. In some examples, the intent handler 210 may ask the user for information missing from one or more slots of an intent template. For example, regarding the phrase "When Gary comes into the room with the others introduce" and its explicitly missing information in the content slot following the word "introduce," the intent handler 210 may broadcast a spoken word query to the user asking "Whom do you want to introduce?" In other examples, the intent handler 210 may query the user via other interfaces, such as by displaying a query on a display device.

When the intent handler 210 receives a response to its query from the user (via the voice listener 206 and parser 208), the intent handler may populate the slot with the response. At this point, the method 600 may return to 602 and the steps following to analyze this newly-added information for any ambiguities as described above.

With reference now to FIG. 6B, at 622 the method 600 may include resolving an ambiguity by analyzing information from a prior conversation turn. In different examples, the method may analyze both utterances as a single or combined utterance, and/or may use one or more elements from a prior utterance to generate one or more slots in an intent template for a current utterance.

In some examples, the intent handler 210 may analyze content from a previous intent template and/or one or more slots of the template. In some examples, the intent handler 210 may determine that a current utterance is additive to a previous utterance. For example, consider the phrase "When Justin is near the oven, alert Erich." Justin may be a toddler, Erich the toddler's father, and the user speaking the phrase may be Justin's mother. The intent handler 210 may receive a first intent template for this phrase. A first resolver may resolve the template and establish a commitment that broadcasts a warning to Erich via Erich's mobile phone when Justin is within 1 meter of the oven in Erich's kitchen.

After speaking this first phrase, Justin's mother may pause for a brief period of time, such as 3 or 4 seconds. After this pause, she may speak a second phrase "and me" which is received by the parser 208. As this phrase contains no action component, the parser 208 may generate a second intent template that has an unknown or unresolved intent. In this example, and because the intent associated with this second phrase is presently unknown, the intent handler 210 may select a second, different resolver to address this second intent template.

Based at least in part on this second phrase beginning with the conjunction "and" followed by the pronoun "me", the second resolver may determine that Justin's mother intends to refer to a prior utterance. The second resolver may utilize an anaphoric resolution technique to associate the word "me" to Justin's mother. By using this data and analyzing the previously-established commitment, the second resolver may determine that the intent associated with the second phrase "and me" is related to the intent associated with the prior phrase "When Justin is near the oven, alert Erich." Accordingly, the second resolver may modify the previously-established commitment to broadcast a warning to both Erich and Justin's mother when Justin is within 1 meter of the oven in the kitchen.

As another example, consider again the phrase "When Justin is near the oven, alert Erich." After speaking this first phrase, Justin's mother may pause for a few seconds and then speak a second phrase "and also if he's close to the pool." As this phrase contains a trigger ("if he's close to the pool") and no action component, the parser 208 may generate a second intent template that has an unknown or unresolved intent. Also, in this example the anaphoric expression "he's" could refer to either of the two names in the preceding phrase (Justin or Erich).

A resolver may determine that it is most probable that the reference to "he" in the trigger of the second phrase is intended to refer to a male person mentioned in another, prior trigger. Based at least in part on this second phrase beginning with the conjunction "and" followed by the words "also" and "if", the second resolver may determine that Justin's mother intends to refer to a prior utterance and to modify a trigger or add another trigger to an action of the previously-established commitment. By using this data and analyzing the previously-established commitment, the second resolver may determine that the intent associated with the second phrase "And also if he's close to the pool" is related to the intent associated with the prior phrase "When Justin is near the oven, alert Erich." Accordingly, the second resolver may modify the previously-established commitment to broadcast a warning to Erich when Justin is either within 1 meter of the oven in the kitchen or within 3 meters of the pool.

In some examples, the intent handler 210 may determine that a current utterance is intended to amend one or more previous utterances. For example, consider the phrase "Please remind me to call Jeff at six o'clock." After speaking this first phrase, the user may pause for a brief moment and then speak a second phrase "I mean Mike." As this phrase contains an ambiguous phrase without a clear trigger or action component, the parser 208 may generate another intent template that has an unresolved intent.

By analyzing the immediately preceding commitment associated with the prior utterance "Please remind me to call Jeff at six o'clock," a resolver may determine that the intent associated with the second phrase "I mean Mike" is most likely related to the intent associated with the prior phrase "Please remind me to call Jeff at six o'clock." Accordingly, this resolver may modify the previously-established commitment to replace the reference to "Jeff" in the action component of this phrase with "Mike."

In another example, consider the phrase "Please remind me to call Jeff and Mike at six o'clock." After speaking this first phrase, the user may pause for a brief moment and then speak a second phrase "not Mike." As this phrase contains an ambiguous phrase without a clear trigger or action component, the parser 208 may generate another intent template that has an unresolved intent.

By analyzing the immediately preceding commitment associated with the utterance "Please remind me to call Jeff and Mike at six o'clock," a resolver may determine that the intent associated with the second phrase "not Mike" is most likely related to the intent associated with the prior phrase "Please remind me to call Jeff and Mike at six o'clock." Accordingly, this resolver may modify the previously-established commitment to remove the reference to "and Mike" from the action component of this phrase.

In some examples, where two or more people are having a conversation, the system may follow the conversation and determine when the active participant (i.e., the person currently speaking) changes in the conversation. In these examples, when the system determines that the current speaker has changed, the system may determine whether the information contained in the new speaker's speech is a continuation of the existing conversation topic/session, or whether a new topic/session has been introduced. Where the new speaker's information is a continuation of the existing conversation topic/session, this determination may be used by the intent handler 210 to resolve ambiguities, complete missing information and/or otherwise clarify the intent of each speaker. For example, such conversation and topic/session tracking may enable the system to assist a team that is working and speaking collaboratively to complete a task. In some examples, the system may track multiple conversations that are occurring simultaneously or otherwise overlapping, and may interact with participants in each conversation as appropriate for each conversation.

In some examples, the intent handler 210 may determine that an intent associated with a newly received phrase is not related to the intent of an immediately preceding commitment. For example, an intent template corresponding to the utterance "Call Justin" may be received and processed by a first resolver into a first commitment. The first resolver may determine that the content slot ("Justin") of the action "Call Justin" is ambiguous because the user has both a Justin Smith and a Justin Doe in the user's contacts database. Accordingly, the first resolver may respond with a query to the user of "Which Justin—Justin Doe or Justin Smith?" In this example, the user responds with an unrelated response, "Please record TV Show A tonight."

The first resolver may analyze this response and its corresponding new intent template by referring to the immediately preceding intent template and its missing content slot. Because the user's response is completely unrelated to the query just presented to the user, the first resolver determines that the new intent template represents a new intent of the user, and thus the new intent template should not be fused with the preceding intent template. Accordingly, the first resolver is replaced by a second resolver that proceeds to analyze the new intent template and establish a new conversation.

At 624 the method 600 may include resolving an alias that refers to a known person or entity by a different name or representation. In one example, a user may refer to "Mimi" in an utterance. The user's contacts database may not contain a contact with the name "Mimi." However, in prior conversations tracked by the intent handler 210, the user's sister may have referred to herself as "Mimi" when speaking with her grandson. A data store accessible to the intent handler 210 may have created an association between the user's sister and the alias "Mimi." By searching the data store for instances of "Mimi" and finding the association between the user's sister and the alias "Mimi", the intent handler 210 may resolve the name "Mimi" in the user's utterance to the user's sister.

At 626 the method 600 may include training the intent handler 210 to associate an alias with a known person or other entity via direct user training input. For example, the user may speak a command, "When I say Mimi I'm referring to my sister Suzanne." The intent handler 210 may create a link between "Mimi" and the user's sister Suzanne, such as by modifying a contacts database file containing information identifying Suzanne.

In a similar manner, at 628 the method 600 may include training the intent handler 210 in a real-time or batch-mode manner to correlate an unrecognized surface form with a newly resolved surface form. For example, the intent handler 210 may be unable to recognize a particular surface form it receives. The intent handler 210 may clarify this surface form via one or more grounding and repairing techniques. In this manner and going forward, the unrecognized surface form subsequently may be correlated with the clarified surface form, whereby the intent handler 210 now may recognize the previously-unrecognized surface form.

In another example, a user may be traveling across New York City in a car for hire. The user may speak a first request to his smartphone, with a middle portion of the phrase unintelligible: "When I get to [unintelligible] call her mobile phone." By analyzing this phrase along with context information, such as motion data indicating the user is traveling in a car, the intent handler 210 may infer that the unintelligible portion of the phrase corresponds to a location slot.

The intent handler 210 may query the user, "Where do you want to do this?" The user may reply with a second response, "Madison." The parser 208 may receive the text "Madison" from the voice listener 206, and may generate a list of the statistically most probable meanings for this word that correspond to the user's actual intent. In this example, the user may have a close friend named Madison, and may have used her name in many spoken requests to the smart assistant device 200. Accordingly, the parser 208 may determine that the user's close friend "Madison" is the most probable intention underlying the user's utterance.

However, based its analysis of the user's first request and other context information, such as the motion data, the intent handler 210 determines that the expected user response to the query "Where do you want to do this?" most likely will be location information. The intent handler also may analyze mapping data that indicates the user will arrive at a Madison Avenue address in five minutes. Accordingly and based at least in part on this context information, the intent handler 210 may not select the user's close friend "Madison", despite the parser's prediction that this is the statistically most probable meaning for this word. Instead, the intent handler may use this context information to resolve this ambiguity by selecting Madison Avenue as the intention of the user.

In some examples where the intent handler is unable to resolve an intent from an utterance, the system may still offer to take one or more actions. For example, if a user makes the declarative statement "Silver looks nice", the system may not understand the user's intent underlying this utterance. Instead of ignoring the user because the system doesn't understand what it should do with the utterance, the system may offer to display photos of silver jewelry, play music, or take some other action.

It will be appreciated that method 600 is provided by way of example and is not meant to be limiting. Therefore, it is to be understood that method 600 may include additional and/or alternative steps relative to those illustrated in FIGS. 6A and 6B. Further, it is to be understood that method 600 may be performed in any suitable order. Further still, it is to be understood that one or more steps may be omitted from method 600 without departing from the scope of this disclosure.

As described above, when the intent handler 210 has sufficiently clarified and resolved the user's intent, a corresponding commitment may be generated and passed to the commitment engine 212 for execution. The word "commitment" as used herein generally refers to a computer-executable data structure that, upon execution, causes the smart assistant device to perform a task or function. In some cases, executing a commitment can include delivering a message to the user. Such a message may be delivered to the user in response to a question or command previously issued to the smart assistant device, for example, thereby representing part of a conversation or interaction between the human user and the smart assistant device. It will be understood that executing a commitment can cause the smart assistant device to perform any number of tasks, and the performance of these tasks may or may not include delivering a message to a human user. For example, executing a commitment can include activating/deactivating a device, altering a set of computer data, performing an online search, conducting an online purchase, etc.

In some cases, the commitment engine 212 may utilize one or more cost functions to determine one or more costs associated with executing or not executing a commitment and, in some examples, with outputting or not outputting a message to the user.

When delivering messages to a human user (e.g., as part of executing a commitment), it is often desirable that the smart assistant device use natural language phrasing that mimics how a human would normally speak to another human. For example, a human user may speak a question directed to the smart assistant device, which may translate the spoken question into a machine-readable natural language input. Upon receiving and processing the natural language input, the smart assistant device may deliver a message to the user in response to the user's question. This interaction will feel more natural to the human user when the smart assistant device's response is phrased in a natural, human-sounding manner, which can encourage the user to make further use of the smart assistant device in the future.

In contrast, a message delivered from the smart assistant device that uses unusual vocabulary or phrasing relative to how ordinary humans converse can feel unnerving to the user, and discourage further interaction with the smart assistant device.

In many cases, a message delivered by the smart assistant device in response to a natural language input can feel more natural when the phrasing of the message is based at least in part on a length of time that has passed since the natural language input was translated from human speech. As an example, a human user may direct a smart assistant device to purchase tickets to a specific event, and ask the smart assistant device to notify the human user when the tickets are purchased. Upon purchasing the tickets, the smart assistant device may deliver a message that states "OK, they've been purchased." If only a short amount of time has passed since the human user requested the purchase, this may feel to the human user like a normal and natural response. However, if a longer amount of time has passed since the human user requested the purchase (e.g., several minutes, hours, or days), this response may be confusing to the user, who may have forgotten what they requested. In another case, upon purchasing the tickets, the smart assistant device may state: "By the way, the tickets you requested earlier have been purchased." This may feel like a normal, natural response to the user when a relatively long amount of time has passed since the user requested the purchase. However, if only a short amount of time has passed (e.g., a few seconds), this response may strike the user as unnecessarily specific and overly verbose.

Figure 7:
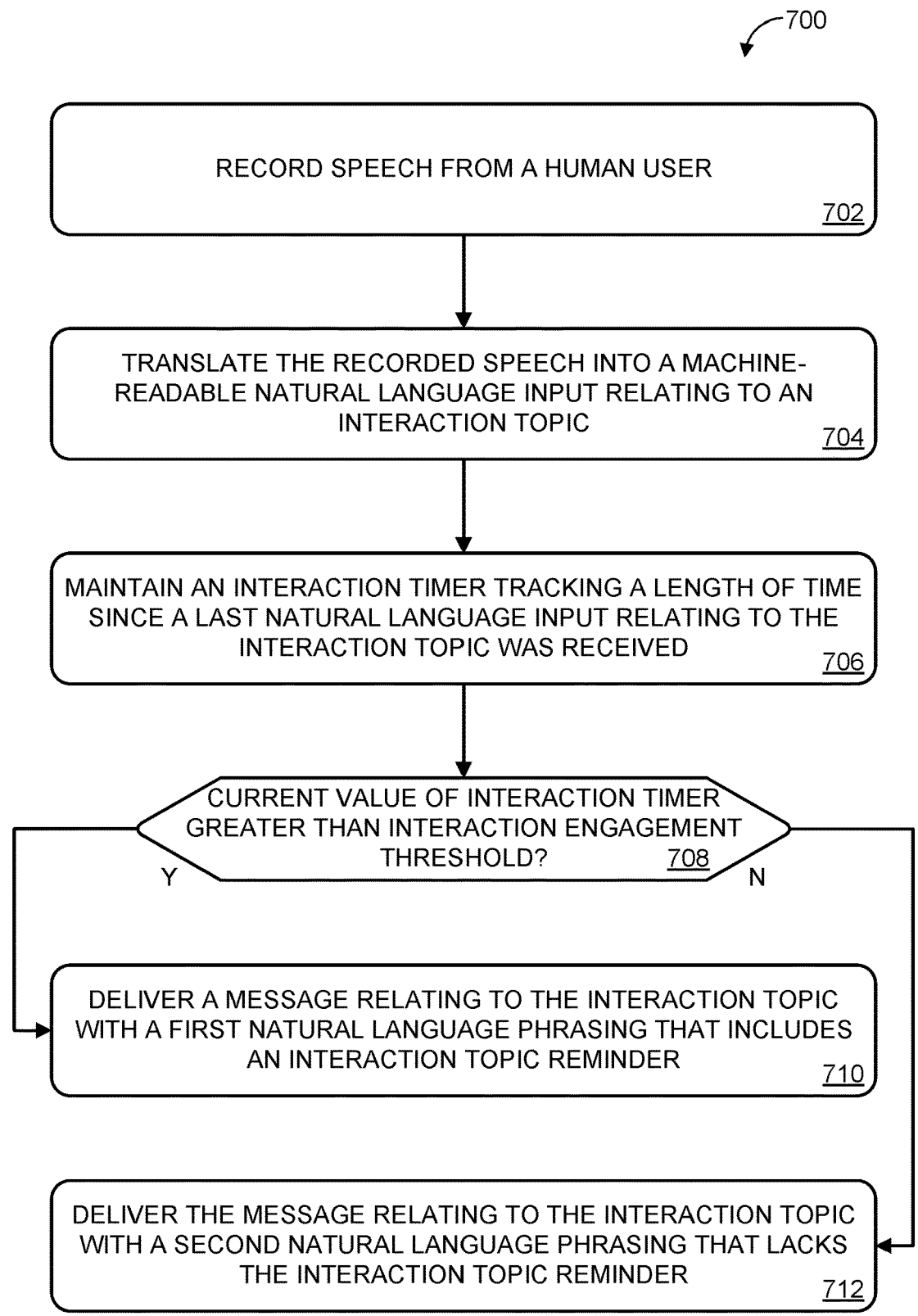
FIG. 7 illustrates an example method for natural language interaction.

Accordingly, FIG. 7 illustrates an example method 700 for natural language interaction that alters message phrasing depending on a length of time that has passed since a last natural language input was received for a given interaction topic. At 702, method 700 includes recording speech provided by a human user. Recorded speech can take the form of spoken words detected via a microphone, but also may take the form of text input via a suitable input interface (e.g., physical or touch-screen keyboard), hand gesture, or brain activity.

At 704, method 700 includes translating the recorded speech into a machine-readable natural language input relating to an interaction topic. As used herein, a "natural language input" refers to the smart assistant device's translation/interpretation of a communication received from a human user. Upon receiving the communication from the human user, the smart assistant device may then perform any suitable processing for deriving a natural language input from the communication. When the user communicates via speaking words out loud, processing the user's communication can include passing detected audio through an analog-to-digital converter (ADC), and analyzing the digital representation of the user's speech to identify specific words spoken by the user. This may be done, for example, by voice listener 206 described above.

Figure 8:
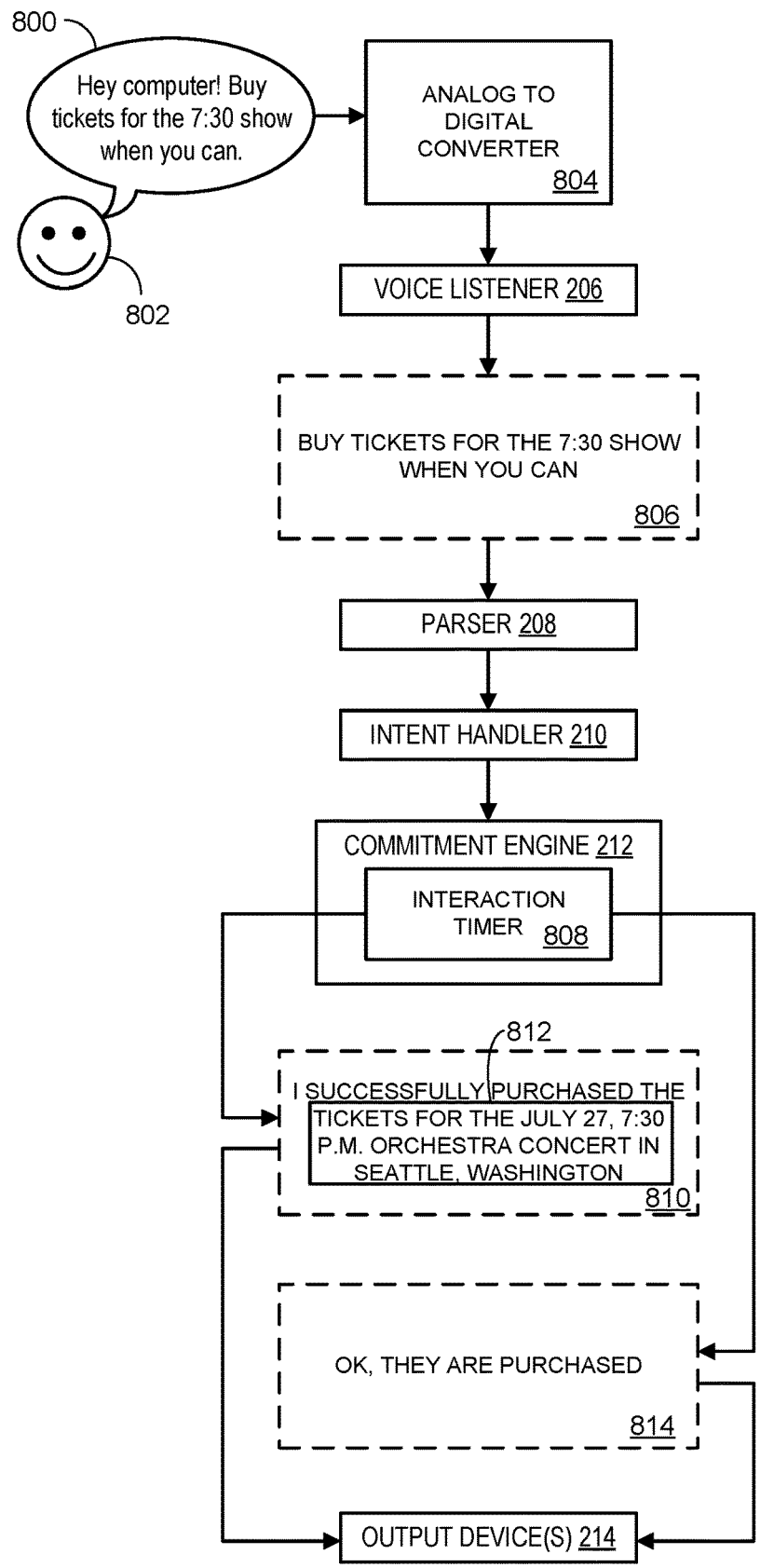
FIG. 8 shows an example flowchart for delivering a message to a human user.

An example interaction between a human user and a smart assistant device is schematically illustrated in FIG. 8, which shows a communication 800 provided by a human user 802. In the example of FIG. 8, communication 800 takes the form of speech spoken aloud by the human user, and the user's speech is detected by the smart assistant device. For example, communication 800 may be detected by microphone 202A of smart assistant device 200, described above with respect to FIG. 2. Upon receipt, communication 800 is passed through an analog-to-digital converter 804, and a digital representation of communication 800 is processed by voice listener 206 to derive a machine-readable natural language input 806 that may, for example, include the smart assistant device's internal prediction of the words spoken by the human user.

Deriving the natural language input from the human user's communication can in some cases include performing various natural language processing steps on the recorded communication to determine an interaction topic of the smart assistant device's current interaction with the human user. As used herein, "interaction topic" refers to the smart assistant device's interpretation or categorization of a human user's goal in interacting with the smart assistant device, and is akin to "user intention" and "user intent" used above. In the example of FIG. 8, natural language processing of the communication is performed by parser 208 and intent handler 210. For example, parser 208 may use natural language input 806 to fill in an intent template, which may then be interpreted by one or more resolvers of intent handler 210, as described above. As a result, the smart assistant device may derive an interaction topic or machine-readable user intent from the natural language input. Once the interaction topic has been determined, the smart assistant device can generate a commitment relating to the interaction topic for storage in commitment engine 212.

Returning briefly to FIG. 7, at 706, method 700 includes maintaining an interaction timer tracking a length of time since a last natural language input relating to the interaction topic was translated. In other words, upon recording a communication from a human user, and translating the communication into a natural language input relating to an interaction topic, the smart assistant device may begin incrementing an interaction timer tracking how long it has been since the user spoke. Each time the user speaks, the smart assistant device may reset the interaction timer to zero. In some cases, the smart assistant device may maintain multiple independent interaction timers relating to different interaction topics. In this manner, the smart assistant device can alter message phrasing depending on how long it has been since a natural language input has been processed for a specific interaction topic, rather than only altering message phrasing based on how long it has been since any natural language input was processed.

In the example of FIG. 8, an interaction timer 808 is maintained by commitment engine 212 of smart assistant device 200. As described above, upon translating the user's communication into natural language input 806, the smart assistant device may begin incrementing interaction timer 808 to track how long it has been since the natural language input was processed. In the event that the smart assistant device derives another natural language input relating to the same interaction topic from an additional communication from the user, interaction timer 808 may be reset to zero. It will be understood that, while FIG. 8 shows the interaction timer implemented as part of commitment engine 212, any suitable component of the smart assistant device may maintain the interaction timer.

Returning to FIG. 7, at 708, method 700 includes determining whether a current value of the interaction timer is greater than an interaction engagement threshold. If YES, method 700 proceeds to 710, which includes delivering a message relating to the interaction topic with a first natural language phrasing that includes an interaction topic reminder. If NO, method 700 proceeds to 712, which includes delivering the message relating to the interaction topic with a second natural language phrasing that lacks the interaction topic reminder. For clarity, the first and second natural language phrasings are referred to herein as the "reminding" and "non-reminding" natural language phrasings, respectively.

In the example of FIG. 8, upon processing the natural language input, the smart assistant device attempts to purchase the user's requested tickets. Upon successfully purchasing the tickets, the smart assistant device conveys this information to the user via a message (i.e., tickets purchased). The specific phrasing used to deliver this message can affect how natural or human-like the interaction feels to the human user, as discussed above. Accordingly, if the current value of the interaction timer is greater than the interaction engagement threshold, the smart assistant device delivers the message with a reminding natural language phrasing 810. In this example, it has been a relatively long time since the user requested the purchase. Accordingly, the reminding natural language phrasing includes an interaction topic reminder 812, explicitly reminding the user that "the tickets for the July 27, 7:30 P.M. orchestra concert in Seattle, Wash." have been purchased, rather than vaguely saying "they are purchased." Conversely, if the current value of the interaction timer is less than the interaction engagement threshold, the smart assistant device delivers the message using a non-reminding natural language phrasing 814 that lacks the interaction topic reminder. In this example, it has been a relatively short amount of time (e.g., a few seconds) since the user requested the purchase, so the user likely does not need to be reminded of their request, and the message simply states "OK, they are purchased."

The present disclosure primarily describes two different natural language phrasings that are used depending on a current value of an interaction timer. However, it will be understood that, in other examples, the smart assistant device may use any suitable number of different natural language phrasings, and can select between the different potential phrasings in any suitable way. For example, in some cases, the smart assistant device may deliver the message using the reminding natural language phrasing when the value of the interaction timer is less than the interaction engagement threshold, and use the non-reminding natural language phrasing when the value of the interaction timer is greater than a second interaction engagement threshold. When the value of the interaction timer is in between the first and second interaction engagement thresholds, the smart assistant device may deliver the message using a third, intermediate natural language phrasing that includes a less-specific interaction topic reminder. To reuse the example from above, the intermediate natural language phrasing may state: "I successfully purchased the tickets for the concert in Seattle." In other cases, the intermediate natural language phrasing may include other suitable levels of specificity.

It will be understood that the message delivered by the smart assistant device, as well as the manner in which the message is delivered, can vary from situation to situation. For example, a message can be delivered audibly, for example via speakers, as visible text on a display, as a notification sent to a personal electronic device of the user, and/or in other suitable ways. Further, the specific content of the message delivered to the user can take any suitable form depending on the interaction topic and the natural language input provided by the user.

The interaction topic reminder included in the reminding natural language phrasing can take a variety of suitable forms. In many cases, the interaction topic reminder will include one or more words explicitly referring to the interaction topic of a previous interaction. In the example of FIG.

8, the interaction topic reminder specifies that the smart assistant device has purchased "the tickets for the July 27, 7:30 orchestra concert," in case the user forgot what he instructed the smart assistant device to buy.

In other examples, the interaction topic reminder can refer to the interaction topic using a proper noun, as opposed to a non-specific pronoun. To use the example of FIG. 1, upon detecting that the user's son has arrived, the smart assistant device can deliver this message with the phrasing "David has arrived," if the interaction timer has a value above the interaction engagement threshold, or the phrasing "He has arrived," if the interaction timer has a value below the interaction engagement threshold. In other words, the reminding natural language phrasing refers to the interaction topic (i.e., the user's son) with a proper noun, while the non-reminding natural language phrasing includes a non-specific pronoun that implicitly refers to the interaction topic.

Because the reminding natural language phrasing is intended to remind the user of an earlier interaction (e.g., requesting purchase of tickets), and thereby includes an interaction topic reminder, the reminding natural language phrasing will generally include more words than the non-reminding natural language phrasing. In some examples, the reminding natural language phrasing can include a summary of a previous interaction. For example, before notifying the user that their requested tickets have been purchased, the smart assistant device can first include a short statement reminding the user that they asked for the purchase in the first place. As an example, the smart assistant device can state: "By the way, this morning you asked me to buy tickets for a show at 7:30. I was able to buy the tickets."

In many cases, a variety of contextual factors can influence whether a smart assistant device's message to a user in response to the user's earlier statement or request sounds natural, or human-like, to the user. As an example, a user may make a request of the smart assistant device while the user is watching television. After a few minutes, the smart assistant device may notify the user that it has fulfilled the request. If the user is still in the same place watching television, it is likely that the user remembers making the request, and will understand the message if the smart assistant device uses a less specific phrasing. In contrast, if the user has moved to a different room and/or started a new activity, it may be more likely that the user has forgotten their request, and the smart assistant device may therefore need to use a more specific phrasing when notifying the user that their request has been fulfilled. In other words, the interaction engagement threshold by which the smart assistant device determines whether to use the reminding or non-reminding natural language phrasing can be dynamically adjusted based on one or more user engagement factors.

In some cases, the identity of the human user who provided the natural language input can serve as a user engagement factor. For example, over repeated interactions with a particular human user, the smart assistant device may test different message phrasings as messages are delivered, and conclude that the particular human user requires interaction topic reminders after shorter lengths of time than other users. Accordingly, relatively smaller interaction engagement thresholds may be used whenever the particular human user interacts with the smart assistant device, as compared to other users that interact with the smart assistant device.

In addition to or instead of adjusting the interaction engagement threshold based on user identity, the threshold can be adjusted based on the interaction topic of the message to be delivered. In other words, for certain interaction topics, longer pauses between user speech and device response can feel natural to the user, while feeling unnatural for other interaction topics. As an example, if a user asks the smart assistant device to help the user locate an object that they have misplaced, it is likely that finding the object is a priority for the user. Accordingly, the user is likely to remember making the request for relatively longer than they might remember making other requests. As an example, upon losing their coat, the user may ask the smart assistant device to help the user locate the coat, even as the user continues to walk from room to room searching for the coat herself. In a different example, the user may ask the smart assistant device to purchase tickets for a specific event. If it takes the smart assistant device several minutes to purchase the tickets, the user may have already forgotten their request, and accordingly will need an interaction topic reminder. In contrast, if it takes the smart assistant device several minutes to locate the user's coat from sensor data, it is likely that the user still remembers asking for help locating the coat. Accordingly, the smart assistant device may notify the user of the coat's location without an interaction topic reminder, for example stating: "I found it, it's under the chair in the living room." In other words, the interaction topic "locate coat" may have a relatively larger interaction engagement threshold than the interaction topic "purchase tickets."

In some cases, an interaction engagement threshold for a particular interaction topic may be adjusted based on determining that a previous interaction (e.g., a different stored commitment) has an interaction topic that may be confusingly similar to the particular interaction topic. As an example, a user may request that the smart assistant device purchase tickets for a specific recreational event (e.g., a concert). On a different occasion, the user may request that the smart assistant device purchase tickets for another reason (e.g., plane tickets for a business trip). If, upon purchasing the concert tickets, the smart assistant device simply states "OK, the tickets have been purchased," then the user may be confused as to whether the concert tickets or the plane tickets have been purchased. Accordingly, upon determining that a message to be delivered to a user has a similar interaction topic to another task, previous interaction, stored commitment, etc., then the smart assistant device may dynamically reduce the interaction engagement threshold. In some cases, the interaction engagement threshold may be reduced to zero, such that the smart assistant device uses a reminding natural language phrasing regardless of the length of time that has passed since the natural language input was translated.

It will be understood that different thresholds may be set for different topics in any suitable manner, and user identity and/or interaction topic may or may not be factored into these thresholds. For example, a variety of other user engagement factors can additionally or alternatively be considered by the smart assistant device. Such user engagement factors can include a current time of day, a language spoken by the human user when providing the natural language input, a current location of the human user, a current activity of the human user, and/or whether the human user is interacting with other humans.

In some cases, the time of day at which the smart assistant device delivers a message can affect the phrasing with which the message should be delivered. To reuse the example from FIG. 1, the user may request that the smart assistant device notify her when her son arrives. If this request is made during the day, it may be relatively more likely that the user remembers making the request than, for example, if the user makes the request at night before going to sleep. In other words, if the son arrives at night after the user has fallen asleep, then the user may be groggy or delirious upon being woken up by the smart assistant device. Accordingly, the user may require an interaction topic reminder to understand the delivered message. In contrast, if the son arrives during the day while the user is awake and alert, the user may not require an interaction topic reminder. Accordingly, a smaller interaction engagement threshold can be used at night, while a larger interaction engagement threshold is used during the day.

Another user engagement factor that can affect message phrasing is the language spoken by the human user when making a statement or request. Depending on cultural and/or linguistic differences between different groups of people, a pause between a user request and a smart assistant device response can sound natural to one group of people, while sounding unnatural to another group of people. This difference can, in some cases, be signified by a language spoken by a human user while interacting with the smart assistant device. Accordingly, the smart assistant device may use relatively smaller interaction engagement thresholds when interacting with humans speaking one language, while using relatively larger interaction engagement thresholds while interacting with humans speaking a different language.

Human user position, or changes in position, can also affect the phrasing used by the smart assistant device when delivering messages. For example, a user may state a request to a smart assistant device that is physically located in the user's living room. If, upon fulfilling the request, the smart assistant device is still in the living room, it is relatively more likely that the user remembers making the request. Conversely, if the user has left the living room, it may be relatively more likely that the user has forgotten their request. Accordingly, in some examples, the interaction engagement threshold may be reduced based on determining that the user has left a local environment of the smart assistant device.

Similarly, a current activity of the human user can also affect message phrasing. To reuse an example from above, the user may state a request to the smart assistant device while the user is watching television. If, upon fulfilling the request, the smart assistant device determines that the user is still watching television, then it may be relatively more likely that the user remembers making the request. Conversely, if the user has begun a new activity, such as cooking or sleeping, it may be relatively less likely that the user remembers making the request. Accordingly, in some examples, the interaction engagement threshold may be reduced based on determining that the human user has begun a new activity since the natural language input was received.

In some cases, the interaction engagement threshold may be decreased each time a user is observed to begin a new activity. The amount by which the threshold is decreased for each new activity can be the same for each activity, or different for different activities. For example, some activities that are deemed to require more of the user's attention (e.g., reading a book) may reduce the interaction engagement threshold by more than other activities that require less of the user's attention (e.g., watching television). In some cases, progressive decreases in the interaction engagement threshold as the user begins new activities can be non-linear. In other words, the first new activity started by the user may decrease the interaction engagement threshold by a relatively large amount, while the second new activity reduces the threshold by a smaller amount, the third new activity reduces the threshold by a yet smaller amount, or vice versa.

In some examples, a human user may interact with the smart assistant device before or while interacting with one or more other humans, for example in person or over the phone. In this case, the user may be relatively more distracted, and therefore less likely to remember their interaction with the smart assistant device, than if the user was not interacting with other humans. In this case, upon delivering a message to the user, the smart assistant device may use a natural language phrasing that includes an interaction topic reminder, even if only a relatively short amount of time has passed. In other words, in some examples, the interaction engagement threshold can be reduced based on determining that the human user is interacting with one or more other humans.

It will be understood that additional or alternative user engagement factors can be used to adjust an interaction engagement threshold. In some cases, adjustment of an interaction engagement threshold can be done via any of a variety of suitable machine learning techniques. In other words, the smart assistant device can, over a series of interactions with one or more different human users, observe how the human users react to messages having different phrasings. In some embodiments, a device may dynamically adjust the engagement threshold over time based on how often a user asks follow-up questions. For example, if a user asks for more detail when a phrasing without a reminder is used, the engagement threshold may be shortened so that a reminder will more quickly be provided the next time the assistant delivers a message relating to that interaction topic. These observations can then be used, for example, to train a machine-learning classifier to set an appropriate interaction engagement threshold for a particular natural language input. Examples of suitable machine learning techniques are described below with respect to the entity tracker.

Figure 9:
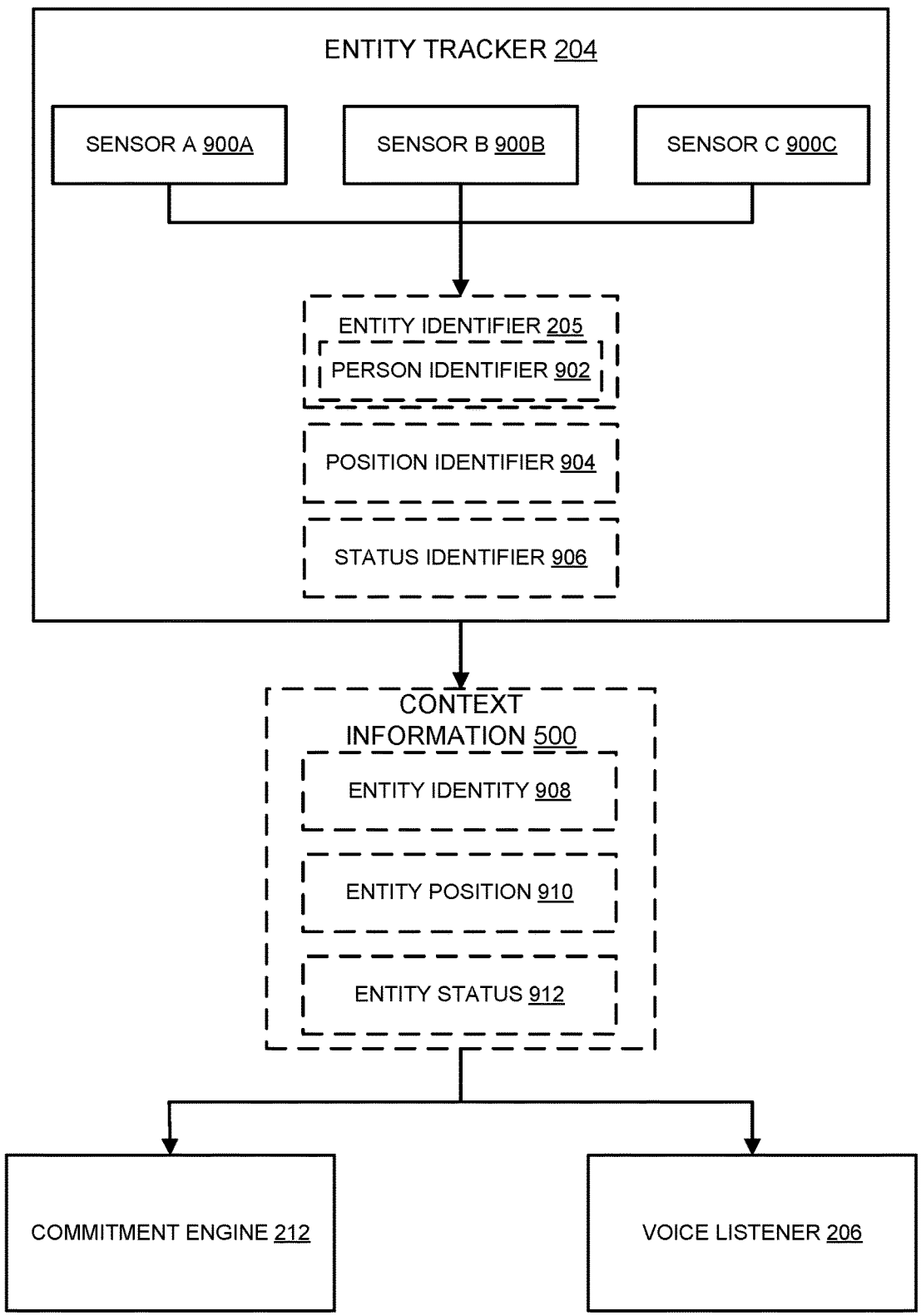
FIG. 9 schematically shows an entity tracker that may determine an identity, position, and/or current status of one or more entities according to examples of the present disclosure.

As indicated above, tracking and identification of humans and other entities in an environment can be performed by an entity tracker. For example, identifying human positions, activities, presence/absence of other humans, etc., as described above can be performed by the entity tracker. FIG. 9 schematically illustrates an example entity tracker 204 that may comprise a component of the smart assistant device 200. Entity tracker 204 may be used to determine an identity, position, and/or current status of one or more entities within range of one or more sensors. Entity tracker 204 may output such information to one or more other modules of smart assistant device 200, such as the commitment engine 212, voice listener 206, etc. Among other uses, such information may be used, for example, to adjust an interaction engagement threshold based on a variety of user engagement factors.

The word "entity" as used in the context of the entity tracker 204 may refer to people, animals, or other living things, as well as non-living objects. For example, the entity tracker may be configured to identify furniture, appliances, structures, landscape features, vehicles, and/or any other physical object, and determine the position/location and current status of such physical objects. In some cases, the entity tracker 204 may be configured to only identify people and not other living or non-living things. In such cases, the word "entity" may be synonymous with the word "person."

Entity tracker 204 receives sensor data from one or more sensors 900, such as sensor A 900A, sensor B 900B, and sensor C 900C, though it will be understood that an entity tracker may be used with any number and variety of suitable sensors. As examples, sensors usable with an entity tracker may include cameras (e.g., visible light cameras, UV cameras, IR cameras, depth cameras, thermal cameras), microphones, pressure sensors, thermometers, motion detectors, proximity sensors, accelerometers, global positioning satellite (GPS) receivers, magnetometers, radar systems, lidar systems, environmental monitoring devices (e.g., smoke detectors, carbon monoxide detectors), barometers, health monitoring devices (e.g., electrocardiographs, sphygmomanometers, electroencephalograms), automotive sensors (e.g., speedometers, odometers, tachometers, fuel sensors), and/or any other sensors or devices that collect and/or store information pertaining to the identity, position, and/or current status of one or more people or other entities. In some examples, the entity tracker 204 may occupy a common device housing with one or more of the plurality of sensors 900, and/or the entity tracker and its associated sensors may be distributed across multiple devices configured to communicate via one or more network communications interfaces (e.g., Wi-Fi adapters, Bluetooth interfaces).

As shown in the example of FIG. 9, entity tracker 204 may include an entity identifier 205, a person identifier 902, a position (location) identifier 904, and a status identifier 906. In some examples, the person identifier 902 may be a specialized component of the entity identifier 205 that is particularly optimized for recognizing people, as opposed to other creatures and non-living things. In other cases, the person identifier 902 may operate separately from the entity identifier 205, or the entity tracker 204 may not include a dedicated person identifier.

Depending on the specific implementation, any or all of the functions associated with the entity identifier, person identifier, position identifier, and status identifier may be performed by the individual sensors 900A-900C. Though the present description generally describes the entity tracker 204 as receiving data from sensors, this does not require that the entity identifier 205, as well as other modules of the entity tracker, must be implemented on a single computing device that is separate and distinct from the plurality of sensors associated with the entity tracker. Rather, functions of the entity tracker 204 may be distributed amongst the plurality of sensors. For example, rather than sending raw sensor data to the entity tracker, individual sensors may be configured to attempt to identify entities that they detect, and report this identification to the entity tracker 204, and/or other modules of smart assistant device 200. In some cases, this identification may include a confidence value.

Each of the entity identifier 205, person identifier 902, position identifier 904, and status identifier 906 is configured to interpret and evaluate sensor data received from the plurality of sensors 900, and to output context information 500 based on the sensor data. Context information 500 may include the entity tracker's guesses/predictions as to an identity, position, and/or status of one or more detected entities based on received sensor data. In some examples, each of the entity identifier 205, person identifier 902, position identifier 904, and status identifier 906 may output their predictions/identifications along with a confidence value indicating a statistical likelihood that the predictions/identifications are correct.

The entity identifier 205, person identifier 902, position identifier 904, status identifier 906, and other processing modules described herein may utilize one or more machine-learning technologies. Non-limiting examples of such machine-learning technologies can include Feedforward Networks, Recurrent Neural Networks (RNN), Long short-term Memory (LSTM), Convolutional neural networks, Support-vector machines (SVM), and Decision Trees. The various identifiers, engines, and other processing blocks described herein may be trained via supervised and/or unsupervised learning utilizing these, or any other appropriate, machine learning technologies to make the described assessments, decisions, identifications, etc. It should be understood, however, that this description is not intended to put forth new technologies for making such assessments, decisions, identifications, etc. Instead, this description is intended to manage computational resources, and as such, is meant to be compatible with any type of processing module.

The entity identifier 205 may output an entity identity 908 of a detected entity, and such entity identity may have any suitable degree of specificity. In other words, based on received sensor data, the entity tracker 204 may predict the identity of a given entity, and output such information as entity identity 908. For example, the entity identifier 205 may report that a particular entity is a piece of furniture, a dog, a human male, etc. Additionally, or alternatively, the entity identifier 205 may report that a particular entity is an oven with a particular model number; a pet dog with a specific name and breed; an owner or user of smart assistant device 200, with the owner/user having a particular name and profile; etc. In some examples, the degree of specificity with which the entity identifier 205 identifies/classifies detected entities may depend on one or more of user preferences and sensor limitations.

When applied to people, the entity tracker 204 may in some cases collect information about individuals whom it is unable to identify by name. For example, the entity identifier 205 may record images of a person's face, and associate these images with recorded audio of the person's voice. Should the person subsequently speak to or otherwise address the smart assistant device 200, the entity tracker 204 will then have at least some information regarding with whom the smart assistant device is interacting. In some examples, the smart assistant device 200 could also prompt the person to state their name, so as to more easily identify the person in the future.

In some examples, the smart assistant device 200 may utilize a person's identity to customize a user interface for the person. In one example, a user may be identified who has limited visual capabilities. In this example and based on this identification, a display of the smart assistant device 200 (or other device with which the user is interacting) may be modified to display larger text, or to provide a voice-only interface.

The position identifier 904 may be configured to output an entity position (i.e., location) 910 of a detected entity. In other words, the position identifier 904 may predict the current position of a given entity based on collected sensor data, and output such information as entity position 910. As with the entity identity 908, the entity position 910 may have any suitable level of detail, and this level of detail may vary with user preferences and/or sensor limitations. For example, the position identifier 904 may report that a detected entity has a two-dimensional position defined on a plane such as a floor or wall. Additionally, or alternatively, the reported entity position 910 may comprise a three-dimensional position of a detected entity within a real world, three-dimensional environment. In some examples an entity position 910 may comprise a GPS position, a location within a mapping system, etc.

The reported entity position 910 for a detected entity may correspond to the entity's geometric center, a particular part of the entity that is classified as being important (e.g., the head of a human), a series of boundaries defining the borders of the entity in three-dimensional space, etc. The position identifier 904 may further calculate one or more additional parameters describing the position and/or orientation of a detected entity, such as a pitch, roll, and/or yaw parameter. In other words, the reported position of a detected entity may have any number of degrees-of-freedom, and may include any number of coordinates defining the position of the entity in an environment. In some examples, an entity position 910 of a detected entity may be reported even if the entity tracker 204 is unable to identify the entity, and/or determine the current status of the entity.

Status identifier 906 may be configured to output an entity status 912 of a detected entity. In other words, the entity tracker 204 may be configured to predict the current status of a given entity based on received sensor data, and output such information as entity status 912. "Entity status" can refer to virtually any measurable or classifiable property, activity, or behavior of a given entity. For example, when applied to a person, the entity status of the person can indicate a posture of the person (e.g., standing, sitting, laying down), a speed at which the person is walking/running, a current activity of the person (e.g., sleeping, watching TV, working, playing a game, swimming, talking on the phone), a current mood of the person (e.g., by evaluating the person's facial expression or tone of voice), biological/physiological parameters of the person (e.g., the person's heart rate, respiration rate, oxygen saturation, body temperature, neurological activity), whether the person has any current or upcoming calendar events/appointments, etc. "Entity status" can refer to additional/alternative properties or behaviors when applied to other creatures or non-living objects, such as a current temperature of an oven or kitchen sink, whether a device (e.g., television, lamp, microwave) is powered on, whether a door is open, etc.

In some examples, the status identifier 906 may use sensor data to calculate a variety of different biological/physiological parameters of a human. This may be done in a variety of suitable ways. For example, the entity tracker 204 may be configured to interface with an optical heart rate sensor, a pulse oximeter, a sphygmomanometer, electrocardiograph, etc. Additionally or alternatively, the status identifier 906 may be configured to interpret data from one or more cameras and/or other sensors in an environment, and process the data in order to calculate a human's heart rate, respiration rate, oxygen saturation, etc. For example, the status identifier 906 may be configured to utilize Eulerian magnification and/or similar techniques to amplify miniscule movements or changes captured by the cameras, thereby allowing the status identifier to visualize the flow of blood through a human's circulatory system and calculate associated physiological parameters. Such information can be used, for example, to determine when the person is asleep, working out, in distress, experiencing health problems, etc.

Upon determining one or more of the entity identity 908, entity position 910, and entity status 912, such information may be sent as context information 500 to any of a variety of external modules or devices, where it may be used in a variety of ways. For example, context information 500 may be used by commitment engine 212 to manage commitments and associated messages and notifications. As described above, context information 500 may be used to adjust an interaction engagement threshold based on one or more user engagement factors. Similarly, context information 500 may be utilized by voice listener 206 when interpreting human speech or activating functions in response to a keyword trigger.

As noted above, in some examples the entity tracker 204 may be implemented in a single computing device. In other examples, one or more functions of the entity tracker 204 may be distributed across multiple computing devices working cooperatively. For example, one or more of the entity identifier 205, person identifier 902, position identifier 904, and status identifier 906 may be implemented on different computing devices, while still collectively comprising an entity tracker configured to perform the functions described herein. As indicated above, any or all of the functions of the entity tracker may be performed by individual sensors 900. Further, in some examples entity tracker 204 may omit one or more of the entity identifier 205, person identifier 902, position identifier 904, and status identifier 906, and/or include one or more additional components not described herein, while still providing context information 500. Additional details regarding components and computing aspects that may be used to implement entity tracker 204 are described in more detail below with respect to FIG. 13.

Each of entity identity 908, entity position 910, and entity status 912 may take any suitable form. For example, each of the entity identity 908, position 114, and status 116 may take the form of a discrete data packet including a series of values and/or labels describing the information gathered by the entity tracker. Each of the entity identity 908, position 910, and status 912 may additionally include a confidence value defining a statistical likelihood that the information is accurate. For example, if the entity identifier 205 receives sensor data that strongly indicates that a particular entity is a human male named "John Smith," then entity identity 908 may include this information along with a corresponding relatively high confidence value, such as 90% confidence. If the sensor data is more ambiguous, then the confidence value included in entity identity 908 correspondingly may be relatively lower, such as 62%. In some examples, separate predictions may be assigned separate confidence values. For example, the entity identity 908 may indicate with 95% confidence that a particular entity is a human male, and indicate with a 70% confidence that the entity is John Smith.

With reference now to FIGS. 10-12, additional example implementations of smart assistant device 200 in a single computing device and across multiple computing devices are illustrated. Additional details regarding components and computing aspects of computing devices illustrated in FIGS. 10-12 are described below with reference to FIG. 13.

FIG. 10 shows an example of an all-in-one computing device 1000 in which the components implementing smart assistant device 200 are arranged together in a standalone device. In some examples, all-in-one computing device 1000 may be communicatively coupled to one or more other computing devices 1002 via a network 1004. In some examples, all-in-one computing device 1000 may be communicatively coupled to a data store 1006 that may store a variety of data, such as user profile data. All-in-one computing device 1000 includes at least one sensor 202, voice listener 206, parser 208, intent handler 210, commitment engine 212, entity tracker 204, and at least one output device 214. Sensor(s) 202 include at least one microphone to receive spoken commands from a user. In some examples one or more other types of sensor(s) 202 also may be included.

As described above, voice listener 206, parser 208, and intent handler 210 work in concert to convert spoken commands or queries into natural language inputs, which can in turn be turned into commitments that are executable by the all-in-one device 1000. The commitment engine 212 stores such commitments, which can serve as the basis for future actions taken and/or messages delivered by the smart assistant device. The entity tracker 204 may provide context information to the commitment engine 212 and/or other modules. At a contextually appropriate time, the commitment engine 212 may execute a commitment and provide output, such as audio signals, to output device(s) 214.

FIG. 11 shows an example implementation in which one or more remote services 1100 perform the natural language processing functionality of smart assistant device 200. In this example, voice listener 206, parser 208, intent handler 210, entity tracker 204 and commitment engine 212 reside on one or more computing devices, such as one or more servers, that are remotely located from a cloud-supported user device A. Sensor data from one or more sensors 202 of the user device A is provided to remote service(s) 1100 via a network. For example, audio data of a user speaking may be captured by a microphone of user device A and provided to voice listener 206.

As described above, voice listener 206, parser 208, and intent handler 210 cooperate to convert the audio data into commitments that are stored in commitment engine 212. At a contextually appropriate time, the commitment engine 212 may execute a commitment and provide output, such as audio signals, to one or more output device(s) 214 of the user device A.

FIG. 12 shows another example implementation in which one or more remote services 1100 perform the natural language processing functionality of smart assistant device 200. In this example, the one or more remote services 1100 are communicatively coupled with a plurality of different sensors 202 and output devices 214. In this example, the sensors include individual standalone sensors A and C, such as microphones, cameras, etc. The output devices include individual standalone output devices B and D, such as loudspeakers.

The one or more remote services 1100 are also communicatively coupled to a device E that includes one or more sensors F and an output device G. Device E may take the form of a simple standalone device comprising a microphone, speaker and network connectivity components. In other examples, device E may be a mobile phone, tablet computer, wall-mounted display, or other suitable computing device. In some examples, device E, sensors A and C, and output devices B and D may be part of the same cloud-supported client. In other examples, any number of individual sensors and devices may be utilized with the one or more remote services 1100.

As described above, the one or more remote services 1100 perform the natural language processing functionality of smart assistant device 200. In some examples, one or more of the remote services 1100 may include all of the natural language processing modules of smart assistant device 200, as shown in the example of FIG. 11. In other examples, one or more remote services 1100 may include less than all of the natural language processing modules, and may be communicatively coupled to the other modules located at one or more other service(s). In the present example, one or more of the remote services 1100 also may comprise a device selector 1200 that may utilize sensor inputs to select output device B, D and/or G to receive output from the commitment engine 212.

In some embodiments, the methods and processes described herein may be tied to a computing system of one or more computing devices. In particular, such methods and processes may be implemented as a computer-application program or service, an application-programming interface (API), a library, and/or other computer-program product.

Figure 13:
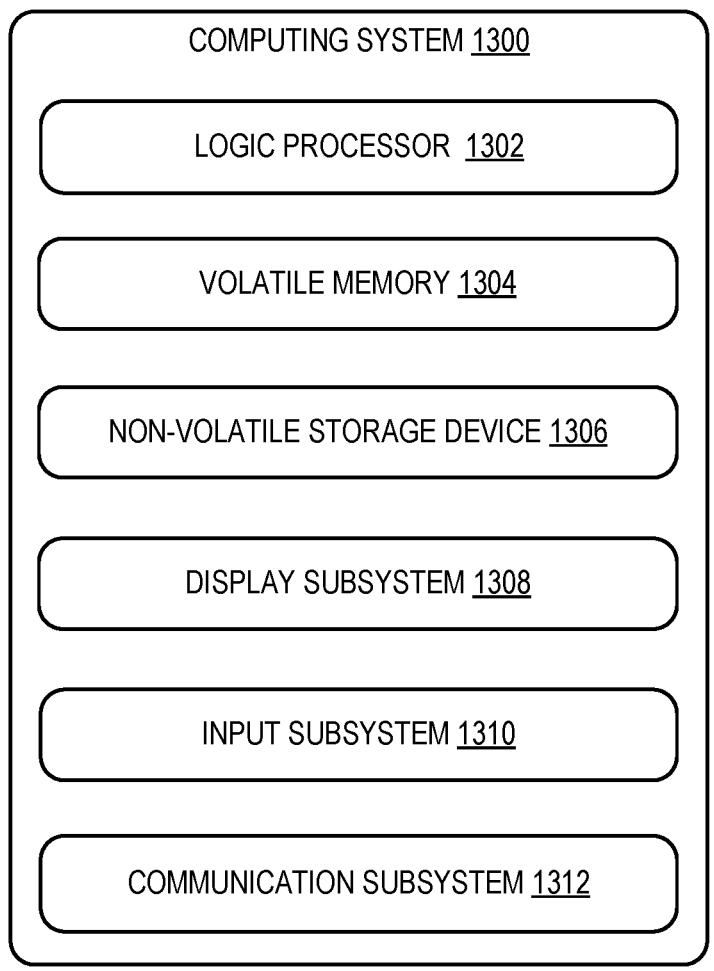
FIG. 13 schematically shows a computing system according to examples of the present disclosure.

FIG. 13 schematically shows a non-limiting embodiment of a computing system 1300 that can enact one or more of the methods and processes described above. Computing system 1300 is shown in simplified form. Computing system 1300 may take the form of one or more personal computers, server computers, tablet computers, home-entertainment computers, network computing devices, gaming devices, mobile computing devices, mobile communication devices (e.g., smartphone), and/or other computing devices.

Computing system 1300 includes a logic processor 1302, volatile memory 1304, and a non-volatile storage device 1306. Computing system 1300 may optionally include a display subsystem 1308, input subsystem 1310, communication subsystem 1312, and/or other components not shown in FIG. 13.

Logic processor 1302 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor 1302 may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 1302 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor 1302 may be virtualized and executed by remotely accessible, networked computing devices configured in a cloud-computing configuration. In such a case, these virtualized aspects may be run on different physical logic processors of various different machines.

Volatile memory 1304 may include physical devices that include random access memory. Volatile memory 1304 is typically utilized by logic processor 1302 to temporarily store information during processing of software instructions. It will be appreciated that volatile memory 1304 typically does not continue to store instructions when power is cut to the volatile memory.

Non-volatile storage device 1306 includes one or more physical devices configured to hold instructions executable by the logic processors to implement the methods and processes described herein. When such methods and processes are implemented, the state of non-volatile storage device 1306 may be transformed—e.g., to hold different data.

Non-volatile storage device 1306 may include physical devices that are removable and/or built-in. Non-volatile storage device 1306 may include optical memory (CD, DVD, HD-DVD, Blu-Ray Disc, etc.), semiconductor memory (ROM, EPROM, EEPROM, FLASH memory, etc.), and/or magnetic memory (hard-disk drive, floppy-disk drive, tape drive, MRAM, etc.), or other mass storage device technology. Non-volatile storage device 1306 may include nonvolatile, dynamic, static, read/write, read-only, sequential-access, location-addressable, file-addressable, and/or content-addressable devices. It will be appreciated that nonvolatile storage device 1306 is configured to hold instructions even when power is cut to the non-volatile storage device.

Aspects of logic processor 1302, volatile memory 1304, and non-volatile storage device 1306 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module", "program" and "engine" may be used to describe an aspect of computing system 1300 implemented to perform a particular function. In some cases, a module, program or engine may be instantiated via logic processor 1302 executing instructions held by non-volatile storage device 1306, using portions of volatile memory 1304. It will be understood that different modules, programs or engines may be instantiated from the same application, service, code block, object, library, routine, API, function, etc. Likewise, the same module, program or engine may be instantiated by different applications, services, code blocks, objects, routines, APIs, functions, etc. The terms modules, programs and engines encompass individual or groups of executable files, data files, libraries, drivers, scripts, database records, etc.

It will be appreciated that a "service", as used herein, is an application program that may be executable across multiple user sessions. A service may be available to one or more system components, programs, and/or other services. In some implementations, a service may run on one or more server-computing devices.

When included, display subsystem 1308 may be used to present a visual representation of data held by non-volatile storage device 1306. As the herein described methods and processes change the data held by the non-volatile storage device, and thus transform the state of the non-volatile storage device, the state of display subsystem 1308 may likewise be transformed to visually represent changes in the underlying data. Display subsystem 1308 may include one or more display devices utilizing virtually any type of technology. Such display devices may be combined with logic processor 1302, volatile memory 1304, and/or non-volatile storage device 1306 in a shared enclosure, or such display devices may be peripheral display devices.

When included, input subsystem 1310 may comprise or interface with one or more user-input devices. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection, gaze detection, and/or intent recognition; electric-field sensing componentry for assessing brain activity; any of the sensors described with respect to the example use cases and environments discussed above; and/or any other suitable sensor.

When included, communication subsystem 1312 may be configured to communicatively couple computing system 1300 with one or more other computing devices. Communication subsystem 1312 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 1300 to send and receive data to and from other devices via a network such as the Internet.

In an example, a method for natural language interaction comprises: recording speech provided by a human user; translating the recorded speech into a machine-readable natural language input relating to an interaction topic; maintaining an interaction timer tracking a length of time since a last machine-readable natural language input relating to the interaction topic; based on a current value of the interaction timer being greater than an interaction engagement threshold, delivering a message relating to the interaction topic with a first natural language phrasing that includes an interaction topic reminder; or based on the current value of the interaction timer being less than the interaction engagement threshold, delivering the message relating to the interaction topic with a second natural language phrasing that lacks the interaction topic reminder. In this example or any other example, the method further comprises performing natural language processing on the recorded speech provided by the human user to ascertain the interaction topic. In this example or any other example, the interaction topic reminder includes one or more words explicitly referring to the interaction topic. In this example or any other example, the interaction topic reminder refers to the interaction topic using at least one proper noun. In this example or any other example, the interaction topic reminder includes a summary of a most recent interaction with the human user relating to the interaction topic. In this example or any other example, the first natural language phrasing includes more words than the second natural language phrasing. In this example or any other example, the second natural language phrasing includes one or more non-specific pronouns that implicitly refer to the interaction topic. In this example or any other example, the interaction engagement threshold is dynamically adjusted based on one or more user engagement factors. In this example or any other example, the one or more user engagement factors include the interaction topic. In this example or any other example, the one or more user engagement factors include a current time of day. In this example or any other example, the one or more user engagement factors include an identity of the human user. In this example or any other example, the one or more user engagement factors include a language spoken by the human user when providing the recorded speech. In this example or any other example, the interaction engagement threshold is reduced based on determining that the human user has left a local environment of a smart assistant device. In this example or any other example, the interaction engagement threshold is reduced based on determining that the human user has begun a new activity since the natural language input was translated. In this example or any other example, the interaction engagement threshold is reduced based on determining that the human user is interacting with one or more other humans.

In an example, a smart assistant device comprises: a logic processor; and a storage device holding instructions executable by the logic processor to: record speech provided by a human user; translate the recorded speech into a machine-readable natural language input relating to an interaction topic; maintain an interaction timer tracking a length of time since a last machine-readable natural language input relating to the interaction topic; based on a current value of the interaction timer being greater than an interaction engagement threshold, deliver a message relating to the interaction topic with a first natural language phrasing that includes an interaction topic reminder; or based on the current value of the interaction timer being less than the interaction engagement threshold, deliver the message relating to the interaction topic with a second natural language phrasing that lacks the interaction topic reminder. In this example or any other example, the interaction topic reminder includes one or more words explicitly referring to the interaction topic. In this example or any other example, the interaction topic reminder refers to the interaction topic using at least one proper noun. In this example or any other example, the second natural language phrasing includes one or more non-specific pronouns that implicitly refer to the interaction topic.

In an example, a method for natural language interaction comprises: recording speech provided by a human user; translating the recorded speech into a machine-readable natural language input relating to an entity; maintaining an interaction timer tracking a length of time since a last machine-readable natural language input referring to the entity; based on a current value of the interaction timer being greater than an interaction engagement threshold, delivering a message relating to the entity to the human user with a first natural language phrasing, the first natural language phrasing referring to the entity with a proper noun; or based on the current value of the interaction timer being less than the interaction engagement threshold, delivering the message relating to the entity to the human user with a second natural language phrasing, the second natural language phrasing implicitly referring to the entity with a non-specific pronoun.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A method for natural language interaction, comprising:
receiving sensor data via a network;
translating the sensor data into a machine-readable natural language input relating to an interaction topic;
maintaining an interaction timer tracking a length of time since a last machine-readable natural language input relating to the interaction topic;
based on a current value of the interaction timer being greater than an interaction engagement threshold, outputting a message relating to the interaction topic with a first natural language phrasing that includes an interaction topic reminder, where the interaction engagement threshold is dynamically adjusted based on one or more user engagement factors; or
based on the current value of the interaction timer being less than the interaction engagement threshold, outputting the message relating to the interaction topic with a second natural language phrasing that lacks the interaction topic reminder.

2. The method of claim 1, where the first natural language phrasing includes more words than the second natural language phrasing.

3. The method of claim 1, where the interaction topic reminder includes a summary of a most recent interaction with a human user relating to the interaction topic.

4. The method of claim 1, where the one or more user engagement factors include the interaction topic.

5. The method of claim 1, where the one or more user engagement factors include a current time of day.

6. The method of claim 1, where the one or more user engagement factors include an identity of a human user who provided the sensor data translated into the machine-readable natural language input.

7. The method of claim 1, where the one or more user engagement factors include a language spoken by a human user when providing the sensor data translated into the machine-readable natural language input.

8. The method of claim 1, where the interaction engagement threshold is reduced based on determining that a human user has left a local environment of a smart assistant device.

9. The method of claim 1, where the interaction engagement threshold is reduced based on determining that a human user has begun a new activity since the sensor data was translated into the machine-readable natural language input.

10. The method of claim 1, where the interaction engagement threshold is reduced based on determining that a human user who provided the sensor data translated into the machine-readable natural language input is interacting with one or more other humans.

11. The method of claim 1, where the second natural language phrasing includes one or more non-specific pronouns that implicitly refer to the interaction topic.

12. The method of claim 1, where the interaction topic reminder includes one or more words explicitly referring to the interaction topic.

13. The method of claim 1, where the interaction topic reminder refers to the interaction topic using at least one proper noun.

14. A method for natural language interaction, comprising:
receiving sensor data;
translating the sensor data into a machine-readable natural language input;
resolving an ambiguity in the machine-readable natural language input to determine an interaction topic;
maintaining an interaction timer tracking a length of time since a last machine-readable natural language input relating to the interaction topic;
based on a current value of the interaction timer being greater than an interaction engagement threshold, outputting a message relating to the interaction topic with a first natural language phrasing that includes an interaction topic reminder, where the interaction engagement threshold is dynamically adjusted based on one or more user engagement factors; or
based on the current value of the interaction timer being less than the interaction engagement threshold, outputting the message relating to the interaction topic with a second natural language phrasing that lacks the interaction topic reminder.

15. The method of claim 14, where resolving the ambiguity in the machine-readable natural language input includes analyzing prior utterances of a human user to identify information missing in the machine-readable natural language input.

16. The method of claim 14, where the first natural language phrasing includes more words than the second natural language phrasing.

17. The method of claim 14, where the interaction topic reminder includes a summary of a most recent interaction with a human user relating to the interaction topic.

18. A computing device, comprising:
a logic machine; and
a storage machine holding instructions executable by the logic machine to:
receive sensor data;
translate the sensor data into a machine-readable natural language input;
maintain an interaction timer tracking a length of time since a last machine-readable natural language input relating to the interaction topic;
based on a current value of the interaction timer being greater than an interaction engagement threshold, output a message relating to the interaction topic with a first natural language phrasing that includes an interaction topic reminder, where the interaction engagement threshold is dynamically adjusted based on one or more user engagement factors; or
based on the current value of the interaction timer being less than the interaction engagement threshold, output the message relating to the interaction topic with a second natural language phrasing that lacks the interaction topic reminder.

* * * * *